US012697154B2

(12) United States Patent
Hatch et al.

(10) Patent No.: US 12,697,154 B2
(45) Date of Patent: Aug. 4, 2026

(54) ANATOMICALLY-FITTED TARSOMETATARSAL BONE PLATE

(71) Applicant: Treace Medical Concepts, Inc., Ponte Vedra, FL (US)

(72) Inventors: Daniel J. Hatch, Greeley, CO (US); Paul Dayton, Ankeny, IA (US); William T. DeCarbo, Pittsburgh, PA (US); Jody McAleer, Jefferson City, MO (US); Robert D. Santrock, Morgantown, WV (US); W. Bret Smith, Durango, CO (US); Mark Erik Easley, Durham, NC (US); Madeline Lindemann, Palm Coast, FL (US); Jason May, St. John's, FL (US); Sean F. Scanlan, Jacksonville, FL (US); John T. Treace, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 306 days.

(21) Appl. No.: 18/173,605

(22) Filed: Feb. 23, 2023

(65) Prior Publication Data

US 2023/0263557 A1 Aug. 24, 2023

Related U.S. Application Data

(60) Provisional application No. 63/313,162, filed on Feb. 23, 2022.

(51) Int. Cl.
*A61B 17/80* (2006.01)
*A61B 17/17* (2006.01)
(Continued)

(52) U.S. Cl.
CPC ...... *A61B 17/8061* (2013.01); *A61B 17/8057* (2013.01); *A61B 17/1728* (2013.01);
(Continued)

(58) Field of Classification Search
CPC ............ A61B 17/8057; A61B 17/8061; A61B 17/8085; A61B 17/80; A61B 17/8014;
(Continued)

(56) References Cited

U.S. PATENT DOCUMENTS 3,664,022 A 5/1972 Small
4,069,824 A 1/1978 Weinstock
(Continued)

FOREIGN PATENT DOCUMENTS

AU 2006252612 B2 4/2012
AU 2009227957 B2 7/2014
(Continued)

OTHER PUBLICATIONS

Treace Medical Concepts. (Nov. 2017). 1st MTP Fusion Surgical Technique. https://salesportal.treace.com/wp-content/uploads/2018/01/LBL-1405-9089-Rev-A-MTP-Fusion-Surgical-Technique.pdf, 1st accessed Apr. 25, 2025 (Year: 2017).*
(Continued)

*Primary Examiner* — Marcela I. Shirsat
(74) *Attorney, Agent, or Firm* — Fredrikson & Byron, P.A.

(57) ABSTRACT

A bone plate can be used to fixate one or more bones. In some examples, a bone plate has first, second, third, and fourth fixation holes. The first and second fixation holes may be located in a distal body region of the bone plate and co-linear with a bridge central longitudinal axis. The third and fourth fixation holes may be located in a proximal body region of the bone plate, with the third fixation hole co-linear with the bridge central longitudinal axis and the fourth
(Continued)

Figure 1B:
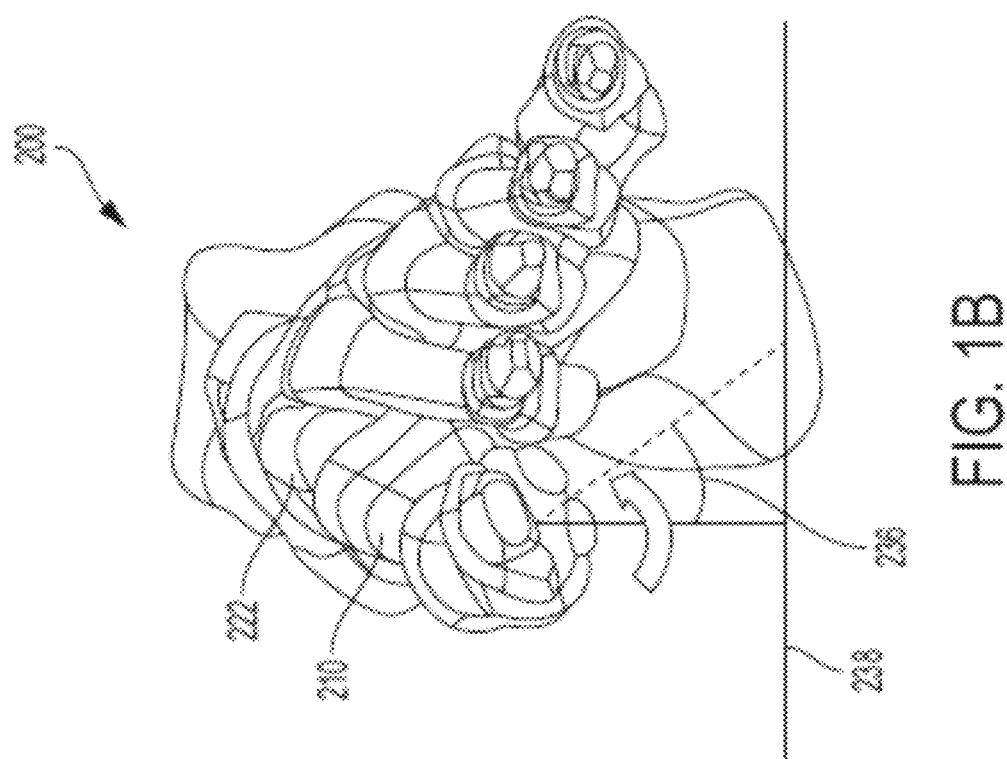

fixation hole offset from the bridge central longitudinal axis in a first plane by a first angle and in a second plane by a second angle.

20 Claims, 17 Drawing Sheets

(51) Int. Cl.

| | |
|---|---|
| *A61B 17/56* | (2006.01) |
| *A61B 17/68* | (2006.01) |
| *A61B 17/84* | (2006.01) |
| *A61B 17/86* | (2006.01) |
| *A61B 17/88* | (2006.01) |
| *A61B 90/00* | (2016.01) |

(52) U.S. Cl.
CPC ... *A61B 2017/564* (2013.01); *A61B 2017/565* (2013.01); *A61B 2017/681* (2013.01); *A61B 17/8014* (2013.01); *A61B 17/8085* (2013.01); *A61B 17/848* (2013.01); *A61B 17/863* (2013.01); *A61B 17/8863* (2013.01); *A61B 2090/037* (2016.02)

(58) Field of Classification Search
CPC ..... A61B 17/17; A61B 17/1728; A61B 17/84; A61B 17/848; A61B 17/86; A61B 17/863; A61B 17/88; A61B 17/8863; A61B 2017/565; A61B 2017/564; A61B 2017/681; A61B 2090/037
USPC .................................................. 606/281, 81
See application file for complete search history.

(56) References Cited

U.S. PATENT DOCUMENTS

| | | | |
|---|---|---|---|
| 4,159,716 A | 7/1979 | Borchers |
| 4,187,840 A | 2/1980 | Watanabe |
| 4,335,715 A | 6/1982 | Kirkley |
| 4,338,927 A | 7/1982 | Volkov et al. |
| 4,349,018 A | 9/1982 | Chambers |
| 4,364,381 A | 12/1982 | Sher et al. |
| 4,409,973 A | 10/1983 | Neufeld |
| 4,440,168 A | 4/1984 | Warren |
| 4,501,268 A | 2/1985 | Comparetto |
| 4,502,474 A | 3/1985 | Comparetto |
| 4,509,511 A | 4/1985 | Neufeld |
| 4,565,191 A | 1/1986 | Slocum |
| 4,570,624 A | 2/1986 | Wu |
| 4,627,425 A | 12/1986 | Reese |
| 4,628,919 A | 12/1986 | Clyburn |
| 4,632,102 A | 12/1986 | Comparetto |
| 4,664,102 A | 5/1987 | Comparetto |
| 4,708,133 A | 11/1987 | Comparetto |
| 4,736,737 A | 4/1988 | Fargie et al. |
| 4,750,481 A | 6/1988 | Reese |
| 4,754,746 A | 7/1988 | Cox |
| 4,757,810 A | 7/1988 | Reese |
| 4,895,141 A | 1/1990 | Koeneman et al. |
| 4,952,214 A | 8/1990 | Comparetto |
| 4,959,065 A | 9/1990 | Arnett et al. |
| 4,959,066 A | 9/1990 | Dunn et al. |
| 4,978,347 A | 12/1990 | Ilizarov |
| 4,988,349 A | 1/1991 | Pennig |
| 4,995,875 A | 2/1991 | Coes |
| 5,021,056 A | 6/1991 | Hofmann et al. |
| 5,035,698 A | 7/1991 | Comparetto |
| 5,042,983 A | 8/1991 | Rayhack |
| 5,049,149 A | 9/1991 | Schmidt |
| 5,053,039 A | 10/1991 | Hofmann et al. |
| 5,078,719 A | 1/1992 | Schreiber |
| 5,112,334 A | 5/1992 | Alchermes et al. |
| 5,147,364 A | 9/1992 | Comparetto |
| 5,176,685 A | 1/1993 | Rayhack |
| 5,207,676 A | 5/1993 | Canadell et al. |
| 5,246,444 A | 9/1993 | Schreiber |
| 5,254,119 A | 10/1993 | Schreiber |
| 5,304,180 A | 4/1994 | Slocum |
| 5,312,412 A | 5/1994 | Whipple |
| 5,358,504 A | 10/1994 | Paley et al. |
| 5,364,402 A | 11/1994 | Mumme et al. |
| 5,374,271 A | 12/1994 | Hwang |
| 5,413,579 A | 5/1995 | Tom Du Toit |
| 5,417,694 A | 5/1995 | Marik et al. |
| 5,449,360 A | 9/1995 | Schreiber |
| 5,470,335 A | 11/1995 | Du Toit |
| 5,490,854 A | 2/1996 | Fisher et al. |
| 5,529,075 A | 6/1996 | Clark |
| 5,540,695 A | 7/1996 | Levy |
| 5,578,038 A | 11/1996 | Slocum |
| 5,586,564 A | 12/1996 | Barrett et al. |
| 5,601,565 A | 2/1997 | Huebner |
| 5,613,969 A | 3/1997 | Jenkins, Jr. |
| 5,620,442 A | 4/1997 | Bailey et al. |
| 5,620,448 A | 4/1997 | Puddu |
| 5,643,270 A | 7/1997 | Combs |
| 5,665,089 A | 9/1997 | Dall et al. |
| 5,667,510 A | 9/1997 | Combs |
| 5,690,639 A | 11/1997 | Lederer et al. |
| 5,702,396 A | 12/1997 | Hoenig et al. |
| H1706 H | 1/1998 | Mason |
| 5,709,686 A | 1/1998 | Talos et al. |
| 5,709,687 A | 1/1998 | Pennig |
| 5,722,978 A | 3/1998 | Jenkins, Jr. |
| 5,749,875 A | 5/1998 | Puddu |
| 5,779,709 A | 7/1998 | Harris, Jr. et al. |
| 5,785,712 A | 7/1998 | Runciman et al. |
| 5,788,695 A | 8/1998 | Richardson |
| 5,803,924 A | 9/1998 | Oni et al. |
| 5,810,822 A | 9/1998 | Mortier |
| 5,843,085 A | 12/1998 | Graser |
| 5,868,749 A | 2/1999 | Reed |
| 5,893,553 A | 4/1999 | Pinkous |
| 5,911,724 A | 6/1999 | Wehrli |
| 5,935,128 A | 8/1999 | Carter et al. |
| 5,941,877 A | 8/1999 | Viegas et al. |
| 5,951,556 A | 9/1999 | Faccioli et al. |
| 5,980,526 A | 11/1999 | Johnson et al. |
| 5,984,931 A | 11/1999 | Greenfield |
| 6,007,535 A | 12/1999 | Rayhack et al. |
| 6,027,504 A | 2/2000 | Mcguire |
| 6,030,391 A | 2/2000 | Brainard et al. |
| 6,162,223 A | 12/2000 | Orsak et al. |
| 6,171,309 B1 | 1/2001 | Huebner |
| 6,183,475 B1 | 2/2001 | Lester et al. |
| 6,203,545 B1 | 3/2001 | Stoffella |
| 6,248,109 B1 | 6/2001 | Stoffella |
| 6,391,031 B1 | 5/2002 | Toomey |
| 6,416,465 B2 | 7/2002 | Brau |
| 6,478,799 B1 | 11/2002 | Williamson |
| 6,511,481 B2 | 1/2003 | Von Hoffmann et al. |
| 6,540,746 B1 | 4/2003 | Bhler et al. |
| 6,547,793 B1 | 4/2003 | Mcguire |
| 6,676,662 B1 | 1/2004 | Bagga et al. |
| 6,706,046 B2 | 3/2004 | Orbay et al. |
| 6,719,773 B1 | 4/2004 | Boucher et al. |
| 6,743,233 B1 | 6/2004 | Baldwin et al. |
| 6,755,838 B2 | 6/2004 | Trnka |
| 6,780,115 B2 | 8/2004 | Schmieding et al. |
| 6,786,909 B1 | 9/2004 | Dransfeld et al. |
| 6,796,986 B2 | 9/2004 | Duffner |
| 6,859,661 B2 | 2/2005 | Tuke |
| 6,964,645 B1 | 11/2005 | Smits |
| 7,018,383 B2 | 3/2006 | Mcguire |
| 7,033,361 B2 | 4/2006 | Collazo |
| 7,037,309 B2 | 5/2006 | Weil et al. |
| 7,097,647 B2 | 8/2006 | Segler |
| 7,112,204 B2 | 9/2006 | Justin et al. |
| 7,153,310 B2 | 12/2006 | Ralph et al. |
| 7,175,667 B2 | 2/2007 | Saunders et al. |
| 7,182,766 B1 | 2/2007 | Mogul |
| 7,229,445 B2 | 6/2007 | Hayeck et al. |

(56) References Cited

U.S. PATENT DOCUMENTS

| | | | |
|---|---|---|---|
| 7,241,298 B2 | 7/2007 | Nemec et al. |
| 7,282,054 B2 | 10/2007 | Steffensmeier et al. |
| 7,344,538 B2 | 3/2008 | Myerson et al. |
| 7,377,924 B2 | 5/2008 | Raistrick et al. |
| 7,465,303 B2 | 12/2008 | Riccione et al. |
| 7,537,596 B2 | 5/2009 | Jensen |
| 7,540,874 B2 | 6/2009 | Trumble et al. |
| 7,572,258 B2 | 8/2009 | Stiernborg |
| 7,578,825 B2 | 8/2009 | Huebner |
| 7,625,381 B2 | 12/2009 | Michelson |
| 7,641,660 B2 | 1/2010 | Lakin et al. |
| D610,257 S | 2/2010 | Horton |
| 7,686,811 B2 | 3/2010 | Byrd et al. |
| 7,691,108 B2 | 4/2010 | Lavallee |
| 7,695,473 B2 | 4/2010 | Ralph et al. |
| 7,722,653 B2 | 5/2010 | Young et al. |
| 7,727,264 B2 | 6/2010 | Orbay et al. |
| 7,763,026 B2 | 7/2010 | Egger et al. |
| 7,785,355 B2 | 8/2010 | Mohr et al. |
| D629,900 S | 12/2010 | Fisher |
| 7,931,680 B2 | 4/2011 | Myerson et al. |
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,746 B2 | 12/2011 | Novak |
| 8,123,753 B2 | 2/2012 | Poncet |
| 8,133,283 B2 | 3/2012 | Wilson |
| 8,137,406 B2 | 3/2012 | Novak et al. |
| 8,147,530 B2 | 4/2012 | Strnad et al. |
| 8,162,996 B2 | 4/2012 | Schelling |
| 8,167,918 B2 | 5/2012 | Strnad et al. |
| 8,172,848 B2 | 5/2012 | Tomko et al. |
| 8,172,884 B2 | 5/2012 | Bouman |
| 8,172,886 B2 | 5/2012 | Castaneda et al. |
| 8,177,819 B2 | 5/2012 | Huebner et al. |
| 8,177,820 B2 | 5/2012 | Anapliotis et al. |
| 8,177,822 B2 | 5/2012 | Medoff |
| 8,192,441 B2 | 6/2012 | Collazo |
| 8,197,487 B2 | 6/2012 | Poncet et al. |
| 8,231,623 B1 | 7/2012 | Jordan |
| 8,231,662 B2 | 7/2012 | Huebner |
| 8,231,663 B2 | 7/2012 | Kay et al. |
| 8,235,994 B2 | 8/2012 | Hollawell |
| 8,236,000 B2 | 8/2012 | Ammann et al. |
| 8,236,034 B2 | 8/2012 | Binder et al. |
| 8,241,338 B2 | 8/2012 | Castaneda et al. |
| 8,246,561 B1 | 8/2012 | Agee et al. |
| 8,246,661 B2 | 8/2012 | Beutter et al. |
| D666,721 S | 9/2012 | Wright et al. |
| 8,257,403 B2 | 9/2012 | Den Hartog et al. |
| 8,257,405 B2 | 9/2012 | Haidukewych et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,303,596 B2 | 11/2012 | Plaky et al. |
| 8,313,492 B2 | 11/2012 | Wong et al. |
| 8,323,289 B2 | 12/2012 | Re |
| 8,337,503 B2 | 12/2012 | Lian |
| 8,343,159 B2 | 1/2013 | Bennett |
| 8,377,105 B2 | 2/2013 | Bscher |
| 8,382,807 B2 | 2/2013 | Austin et al. |
| 8,398,687 B2 | 3/2013 | Vasta et al. |
| 8,403,966 B2 | 3/2013 | Ralph et al. |
| D679,395 S | 4/2013 | Wright et al. |
| 8,409,209 B2 | 4/2013 | Ammann et al. |
| 8,435,246 B2 | 5/2013 | Fisher et al. |
| 8,444,679 B2 | 5/2013 | Ralph et al. |
| 8,475,462 B2 | 7/2013 | Thomas et al. |
| 8,496,662 B2 | 7/2013 | Novak et al. |
| 8,496,690 B2 | 7/2013 | Sixto et al. |
| 8,512,339 B2 | 8/2013 | Medoff et al. |
| 8,518,045 B2 | 8/2013 | Szanto |
| 8,523,870 B2 | 9/2013 | Green et al. |
| 8,529,571 B2 | 9/2013 | Horan et al. |
| 8,529,608 B2 | 9/2013 | Terrill et al. |
| 8,540,777 B2 | 9/2013 | Ammann et al. |
| 8,545,508 B2 | 10/2013 | Collazo |
| 8,545,540 B2 | 10/2013 | Castaneda et al. |
| D694,884 S | 12/2013 | Mooradian et al. |
| D695,402 S | 12/2013 | Dacosta et al. |
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| 8,702,762 B2 | 4/2014 | Jacene et al. |
| D705,929 S | 5/2014 | Frey |
| 8,715,363 B2 | 5/2014 | Ratron et al. |
| 8,728,084 B2 | 5/2014 | Berelsman et al. |
| 8,734,492 B2 | 5/2014 | Mohr et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,764,807 B2 | 7/2014 | Michel et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,784,498 B2 | 7/2014 | Scheland |
| 8,795,286 B2 | 8/2014 | Sand et al. |
| 8,801,727 B2 | 8/2014 | Chan et al. |
| 8,808,303 B2 | 8/2014 | Stemniski et al. |
| 8,808,334 B2 | 8/2014 | Strnad et al. |
| 8,828,012 B2 | 9/2014 | May et al. |
| 8,828,063 B2 | 9/2014 | Blitz et al. |
| 8,834,532 B2 | 9/2014 | Velikov et al. |
| 8,834,537 B2 | 9/2014 | Castaneda et al. |
| 8,852,249 B2 | 10/2014 | Ahrens et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| 8,888,824 B2 | 11/2014 | Austin et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,940,026 B2 | 1/2015 | Hilse et al. |
| 8,940,029 B2 | 1/2015 | Leung et al. |
| 8,945,132 B2 | 2/2015 | Play et al. |
| 8,998,903 B2 | 4/2015 | Price et al. |
| 8,998,904 B2 | 4/2015 | Zeetser et al. |
| 9,011,507 B2 | 4/2015 | Schelling |
| 9,023,052 B2 | 5/2015 | Lietz et al. |
| 9,044,250 B2 | 6/2015 | Olsen et al. |
| 9,060,822 B2 | 6/2015 | Wright et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| 9,138,244 B2 | 9/2015 | Mebarak et al. |
| D740,424 S | 10/2015 | Dacosta et al. |
| 9,149,313 B2 | 10/2015 | Strnad et al. |
| 9,220,515 B2 | 12/2015 | Castaneda et al. |
| 9,271,769 B2 | 3/2016 | Batsch et al. |
| D765,844 S | 9/2016 | Dacosta |
| D766,434 S | 9/2016 | Dacosta |
| D766,437 S | 9/2016 | Dacosta |
| D766,438 S | 9/2016 | Dacosta |
| D766,439 S | 9/2016 | Dacosta |
| 9,452,057 B2 | 9/2016 | Dacosta et al. |
| 9,522,023 B2 | 12/2016 | Haddad et al. |
| 9,592,084 B2 | 3/2017 | Grant |
| 9,597,130 B2 | 3/2017 | Pappalardo et al. |
| 9,622,805 B2 | 4/2017 | Santrock et al. |
| 9,642,656 B2 | 5/2017 | Kotuljac et al. |

(56)          References Cited

U.S. PATENT DOCUMENTS

| | | | |
|---|---|---|---|
| 9,668,793 B2 | 6/2017 | Gaudin |
| 9,750,538 B2 | 9/2017 | Soffiatti et al. |
| 9,785,747 B2 | 10/2017 | Geebelen |
| 9,867,642 B2 | 1/2018 | Simon |
| 9,936,994 B2 | 4/2018 | Smith et al. |
| 9,980,760 B2 | 5/2018 | Dacosta et al. |
| 10,028,750 B2 | 7/2018 | Rose |
| 10,064,631 B2 | 9/2018 | Dacosta et al. |
| 10,159,499 B2 | 12/2018 | Dacosta et al. |
| 10,226,287 B2 | 3/2019 | Langford et al. |
| 10,238,437 B2 | 3/2019 | Simon |
| 10,292,713 B2 | 5/2019 | Fallin et al. |
| 10,327,829 B2 | 6/2019 | Dacosta et al. |
| 10,335,220 B2 | 7/2019 | Smith et al. |
| 10,342,590 B2 | 7/2019 | Bays et al. |
| 10,376,268 B2 | 8/2019 | Fallin et al. |
| 10,470,779 B2 | 11/2019 | Fallin et al. |
| 10,575,862 B2 | 3/2020 | Bays et al. |
| 10,729,453 B2 | 8/2020 | Woodard et al. |
| 10,779,867 B2 | 9/2020 | Penzimer et al. |
| 10,856,886 B2 | 12/2020 | Dacosta et al. |
| 10,856,918 B2 | 12/2020 | Dacosta |
| 10,939,939 B1 | 3/2021 | Gil et al. |
| 11,058,467 B2 | 7/2021 | Lueth et al. |
| 11,116,558 B2 | 9/2021 | Smith et al. |
| 11,141,204 B2 | 10/2021 | Davison et al. |
| 11,160,590 B2 | 11/2021 | Davison et al. |
| 11,213,327 B2 | 1/2022 | Gault et al. |
| 11,278,332 B2 | 3/2022 | Davison et al. |
| 11,304,705 B2 | 4/2022 | Fallin et al. |
| 11,304,735 B2 | 4/2022 | Sayger et al. |
| 11,571,312 B1 | 2/2023 | Parekh et al. |
| 11,931,106 B2 | 3/2024 | Perler et al. |
| 11,957,390 B2 | 4/2024 | Sidebotham et al. |
| 11,986,251 B2 | 5/2024 | Perler et al. |
| 2002/0058944 A1 | 5/2002 | Michelson |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2003/0060827 A1 | 3/2003 | Coughln |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0116930 A1 | 6/2004 | O'Driscoll et al. |
| 2004/0138669 A1 | 7/2004 | Horn |
| 2005/0004676 A1 | 1/2005 | Schon et al. |
| 2005/0019257 A1 | 1/2005 | Kim et al. |
| 2005/0033430 A1 | 2/2005 | Powers et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde |
| 2005/0273112 A1 | 12/2005 | Mcnamara |
| 2006/0036257 A1 | 2/2006 | Steffensmeier |
| 2006/0116679 A1 | 6/2006 | Lutz et al. |
| 2006/0129163 A1 | 6/2006 | Mcguire |
| 2006/0149264 A1 | 7/2006 | Castaneda et al. |
| 2006/0173459 A1 | 8/2006 | Kay et al. |
| 2006/0206044 A1 | 9/2006 | Simon |
| 2006/0217733 A1 | 9/2006 | Plassky et al. |
| 2006/0229621 A1 | 10/2006 | Cadmus |
| 2006/0235397 A1 | 10/2006 | Sanders et al. |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2006/0276795 A1 | 12/2006 | Orbay et al. |
| 2007/0010818 A1 | 1/2007 | Stone et al. |
| 2007/0123857 A1 | 5/2007 | Deffenbaugh et al. |
| 2007/0123884 A1 | 5/2007 | Abdou |
| 2007/0191848 A1 | 8/2007 | Wack et al. |

| | | | |
|---|---|---|---|
| 2007/0233106 A1* | 10/2007 | Horan | A61B 17/8061 |
| | | | 606/282 |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015591 A1 | 1/2008 | Castaneda et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0112212 A1 | 4/2009 | Murray et al. |
| 2009/0118733 A1 | 5/2009 | Orsak et al. |
| 2009/0118768 A1 | 5/2009 | Sixto, Jr. et al. |
| 2009/0198244 A1 | 8/2009 | Leibel |
| 2009/0198279 A1 | 8/2009 | Zhang et al. |
| 2009/0210010 A1 | 8/2009 | Strnad et al. |
| 2009/0210013 A1 | 8/2009 | Kay et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0281543 A1 | 11/2009 | Orbay et al. |
| 2009/0287309 A1 | 11/2009 | Walch et al. |
| 2009/0306675 A1 | 12/2009 | Wong et al. |
| 2010/0004691 A1 | 1/2010 | Amato et al. |
| 2010/0023010 A1 | 1/2010 | Nelson et al. |
| 2010/0069910 A1 | 3/2010 | Hasselman |
| 2010/0121334 A1 | 5/2010 | Couture et al. |
| 2010/0125300 A1* | 5/2010 | Blitz | A61B 17/8085 |
| | | | 606/283 |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0008745 A1 | 1/2011 | Mcquillan et al. |
| 2011/0009865 A1 | 1/2011 | Orfaly |
| 2011/0087295 A1 | 4/2011 | Kubiak et al. |
| 2011/0093017 A1 | 4/2011 | Prasad et al. |
| 2011/0093084 A1 | 4/2011 | Morton |
| 2011/0118739 A1 | 5/2011 | Tyber et al. |
| 2011/0137351 A1 | 6/2011 | Huebner et al. |
| 2011/0166607 A1 | 7/2011 | Castaneda et al. |
| 2011/0178524 A1 | 7/2011 | Lawrence et al. |
| 2011/0245835 A1 | 10/2011 | Dodds et al. |
| 2011/0264149 A1 | 10/2011 | Pappalardo et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265204 A1 | 10/2012 | Schmierer et al. |
| 2012/0265301 A1 | 10/2012 | Demers et al. |

(56) References Cited

U.S. PATENT DOCUMENTS

| | | |
|---|---|---|
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0012952 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0090695 A1 | 4/2013 | Bernstein et al. |
| 2013/0096563 A1 | 4/2013 | Meade et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Wright et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0238032 A1 | 9/2013 | Schilter |
| 2013/0261670 A1 | 10/2013 | Laeng et al. |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0012887 A1 | 1/2014 | Tamano |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0052193 A1 | 2/2014 | Prandi et al. |
| 2014/0074099 A1 | 3/2014 | Vigneron et al. |
| 2014/0074101 A1 | 3/2014 | Collazo |
| 2014/0081341 A1 | 3/2014 | Lin et al. |
| 2014/0094861 A1 | 4/2014 | Fallin |
| 2014/0094924 A1 | 4/2014 | Hacking et al. |
| 2014/0107650 A1 | 4/2014 | Dacosta et al. |
| 2014/0107798 A1 | 4/2014 | Jeng et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0172021 A1 | 6/2014 | Castaneda et al. |
| 2014/0180342 A1 | 6/2014 | Lowery et al. |
| 2014/0180343 A1 | 6/2014 | Gaudin |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0214093 A1 | 7/2014 | Courtney et al. |
| 2014/0249537 A1 | 9/2014 | Wong et al. |
| 2014/0257291 A1 | 9/2014 | Houff |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2015/0032168 A1 | 1/2015 | Orsak et al. |
| 2015/0039033 A1 | 2/2015 | Biedermann |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Anderson et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2015/0250514 A1 | 9/2015 | Terrill et al. |
| 2015/0313652 A1 | 11/2015 | Burckhardt et al. |
| 2015/0335366 A1 | 11/2015 | Dacosta et al. |
| 2015/0359580 A1 | 12/2015 | Dacosta et al. |
| 2016/0015426 A1 | 1/2016 | Dayton |
| 2016/0022315 A1 | 1/2016 | Soffiatti et al. |
| 2016/0030098 A1 | 2/2016 | Dacosta et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0235454 A1 | 8/2016 | Treace et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0338697 A1 | 11/2016 | Biedermann et al. |
| 2016/0354127 A1 | 12/2016 | Lundquist et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1* | 2/2017 | Bays ............... A61B 17/8061 |
| 2017/0056031 A1 | 3/2017 | Awtrey et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2017/0172638 A1 | 6/2017 | Santrock et al. |
| 2017/0360488 A1* | 12/2017 | Kowalczyk ......... A61B 17/809 |
| 2018/0132868 A1 | 5/2018 | Dacosta et al. |
| 2018/0289379 A1 | 10/2018 | Dacosta et al. |
| 2018/0344334 A1 | 12/2018 | Kim et al. |
| 2018/0344371 A1 | 12/2018 | Monk et al. |
| 2019/0357950 A1 | 11/2019 | Bernstein et al. |
| 2020/0015865 A1 | 1/2020 | Lamm et al. |
| 2020/0015874 A1 | 1/2020 | Hartson et al. |
| 2020/0229828 A1 | 7/2020 | Wagner et al. |
| 2020/0237387 A1 | 7/2020 | Luttrell et al. |
| 2020/0330109 A1 | 10/2020 | Woodard et al. |
| 2021/0077192 A1 | 3/2021 | Perler et al. |
| 2021/0338450 A1 | 11/2021 | Hollis et al. |
| 2022/0409222 A1 | 12/2022 | Cundiff et al. |
| 2023/0142406 A1 | 5/2023 | Amiot et al. |
| 2023/0149031 A1 | 5/2023 | Woodard et al. |
| 2023/0255651 A1 | 8/2023 | Cundiff et al. |

FOREIGN PATENT DOCUMENTS

| | | |
|---|---|---|
| CA | 2491824 A1 | 9/2005 |
| CA | 2854997 A1 | 5/2013 |
| CA | 2715491 C | 4/2014 |
| CH | 695846 A5 | 9/2006 |
| CN | 2701408 Y | 5/2005 |
| CN | 2930668 Y | 8/2007 |
| CN | 201558162 U | 8/2010 |
| CN | 101836888 A | 9/2010 |
| CN | 201572172 U | 9/2010 |
| CN | 201586060 U | 9/2010 |
| CN | 201912210 U | 8/2011 |
| CN | 102755186 A | 10/2012 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |

(56) References Cited

FOREIGN PATENT DOCUMENTS

| | | | |
|---|---|---|---|
| CN | 103735306 A | 4/2014 |
| CN | 102860860 B | 5/2014 |
| CN | 203576647 U | 5/2014 |
| CN | 103892954 A | 7/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2389884 B1 | 7/2013 |
| EP | 2441406 B1 | 9/2013 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| EP | 3023068 A2 | 5/2016 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 231718 A | 4/1925 |
| GB | 2154143 A | 9/1985 |
| GB | 2154144 A | 9/1985 |
| GB | 2334214 B | 1/2003 |
| IL | 184773 A | 9/2012 |
| IN | 200904479 P2 | 5/2010 |
| IN | 200903719 P1 | 9/2010 |
| IN | 140/DELNP/2012 P1 | 2/2013 |
| JP | S63005739 A | 1/1988 |
| JP | H05031116 A | 2/1993 |
| JP | H07313522 A | 12/1995 |
| JP | 2004174265 A | 6/2004 |
| JP | 2006158972 A | 6/2006 |
| JP | 4134243 B2 | 8/2008 |
| JP | 2008537498 A | 9/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| KR | 101081268 B1 | 11/2011 |
| MD | 756 B1 | 7/1997 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 03075775 A1 | 9/2003 |
| WO | 2004024009 A1 | 3/2004 |
| WO | 2004089227 A2 | 10/2004 |
| WO | 2006065512 A1 | 6/2006 |
| WO | 2007006430 A1 | 1/2007 |
| WO | 2007106962 A1 | 9/2007 |
| WO | 2008029142 A2 | 3/2008 |
| WO | 2008029143 A2 | 3/2008 |
| WO | 2008051064 A1 | 5/2008 |
| WO | 2009029798 A1 | 3/2009 |
| WO | 2009032101 A2 | 3/2009 |
| WO | 2009158522 A1 | 12/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015094410 A1 | 6/2015 |
| WO | 2015105880 A1 | 7/2015 |
| WO | 2015127515 A2 | 9/2015 |
| WO | 2016003477 A1 | 1/2016 |
| WO | 2016134160 A1 | 8/2016 |
| WO | 2020180598 A1 | 9/2020 |
| ZA | 200808914 A | 2/2012 |

OTHER PUBLICATIONS

Odenbring et al., "A guide instrument for high tibial osteotomy," Acta Orthopaedica Scandinavica, vol. 60, No. 4, 1989, pp. 449-451.

Otsuki et al., "Developing a novel custom cutting guide for curved per-acetabular osteotomy," International Orthopaedics (SICOT), vol. 37, 2013, pp. 1033-1038.

Peters et al., "Flexor Hallucis Longus Tendon Laceration as a Complication of Total Ankle Arthroplasty," Foot & Ankle International, vol. 34, No. 1, 2013, pp. 148-149.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Osteomed, "ExtremiLock Ankle Plating System," Brochure, published prior to Nov. 20, 2014, 6 pages.

Osteomed, "ExtremiLock Foot Plating System," Brochure, published prior to Nov. 20, 2014, 6 pages.

Osteomed, "Hand Plating System," Brochure, published prior to Nov. 20, 2014, 8 pages.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Plaass et al, "Anterior Double Plating for Rigid Fixation of Isolated Tibiotalar Arthrodesis," Foot and Ankle International, vol. 30, No. 7, Jul. 2009, pp. 631-639.

Plaass et al., "Placement of Plantar Plates for Lapidus Arthrodesis: Anatomical Considerations," Foot and Ankle International, vol. 37, No. 4, Apr. 2016, pp. 427-432.

(56) References Cited

OTHER PUBLICATIONS

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Rochet et al., "Proximal Ulna Comminuted Fractures: Fixation Using a Double-Plating Technique," Revue de Chirurgie Orthopdique et Traumatologique, vol. 96, No. 7, Nov. 2010, pp. 800-807.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Schon et al., "Cuneiform-Metatarsal Arthrodesis for Hallux Valgus," The Foot and Ankle, Second Edition, Chapter 8, 2002, pp. 99-117.

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Shurnas et al., "Proximal Metatarsal Opening Wedge Osteotomy," Operative Techniques in Foot and Ankle Surgery, Section I, Chapter 13, 2011, pp. 73-78.

Siddiqui et al. "Fixation Of Metatarsal Fracture With Bone Plate In A Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simpson et al., "Computer-Assisted Distraction Ostegogenesis By Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Smith & Nephew, Inc, "D-RAD Smart Pack," Single-Use Volar Distal Radius Plating System, Brochure, Jun. 2014, 8 pages.

Smith & Nephew, Inc, "EVOS Mini," Plating System, Brochure, May 2015, 12 pages.

Smith & Nephew, Inc, "Medial Column Fusion for Midfoot Deformity Correction," VLP Foot Variable Angle Locked Plating System, Surgical Technique, 2013, 20 pages.

Smith & Nephew, Inc, "Proximal Humerus Locking Plate," Peri-Loc Upper Extremity Locked Plating System, Surgical Technique, Sep. 2006, 36 pages.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Sokoloff, "Lapidus Procedure," Textbook of Bunion Surgery, Chapter 15, 1981, pp. 277-287.

Stableloc External Fixation System, Acumed, Product Overview, Effective date Sep. 2015, 4 pages.

Stahl et al., "Derotation Of Post-Traumatic Femoral Deformities By Closed Intramedullary Sawing," Injury, vol. 37, No. 2, Feb. 2006, pp. 145-151, (Abstract Only).

Stamatis et al., "Mini Locking Plate as Medial Buttress for Oblique Osteotomy for Hallux Valgus," Foot & Ankle International, vol. 31, No. 10, Oct. 2010, pp. 920-922.

Stryker, "Anchorage Plating System," Operative Technique, Rev. 2, Aug. 2015, 32 pages.

Stryker, "VariAx Foot Locked Plating System," Jun. 2008, 25 pages.

Synthes, "LCP Periprosthetic System," 2009, 8 pages.

Talbot et al., "Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Tornier, "CalcLock Extreme," Retrieved from < http://www.tornier-us.com/lower/foot/footra011/>, 2014, 2 pages.

Tornier, "CoverLoc Volar Plate," Retrieved from < http://www.tornier-us.com/upper/hand/writra003/>, 2016, 2 pages.

Tornier, "DFX Distal Fibula and DTX Distal Tibia Plates," Retrieved from < http://www.tornier-us.com/lower/ankle/ anktra003/>, 2016, 2 pages.

Tornier, "Hand and Wrist," Retrieved from <http://www.tornier-us.com/upper/hand/>, 2016, 1 page.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Stewart, "Use for BME Speed Nitinol Staple Fixation for the Lapidus Procedure, date unknown, 1 page."

Nagy et al., "The AO Ulnar Shortening Osteotomy System Indications and Surgical Technique," Journal of Wrist Surgery, vol. 3, No. 2, 2014, pp. 91-97.

Fishco, "A Straightforward Guide To The Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.

Garthwait, "Accu-Cut System Facilitates Enhanced Precision," Podiatry Today, vol. 18, No. 6, Jun. 2005, 6 pages.

Gerard et al., "The Modified Lapidus Procedure," Orthopedics, vol. 31, No. 3, Mar. 2008, 7 pages.

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems fr die Knieendoprothetik," Forschungsberichte, Technische Universitat Munchen, 165, 2002, 11 pages, including partial English Translation.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).

Groves, "Functional Position Joint Sectioning: Pre-Load Method for Lapidus Arthrodesis," The Podiatry Institute, Update 2015, Chapter 6, 2015, pp. 23-29.

(56) References Cited

OTHER PUBLICATIONS

Groves, "Operative Report," St. Tammany Parish Hospital, Date of Procedure, Mar. 26, 2014, 2 pages.

Hardy et al., "Observations on Hallux Valgus," The Journal of Bone and Joint Surgery, vol. 33B, No. 3, Aug. 1951,pp. 376-391.

Hatch et al., "Triplane Hallux Abducto Valgus Classification," The Journal of Foot & Ankle Surgery, vol. 57, No. 5, Sep./Oct. 2018, published online: May 18, 2018, pp. 972-981.

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Horton et al., "Deformity Correction and Arthrodesis of the Midfoot with a Medial Plate," Foot & Ankle, vol. 14, No. 9, Nov./Dec. 1993, pp. 493-499.

Integra, "Integra Large Qwix Positioning and Fixation Screw, Surgical Technique," 2012, 16 pages.

International Searching Authority, "International Search Report and Written Opinion" , From Application No. PCT/US2023/063156, Mailed Sep. 5, 2023, pp. 12.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Magin, "Computernavigierter Gelenkersatz am Knie mit dem Orthopilot," Operative Orthopdie und Traumatologie, vol. 22, No. 1, 2010, pp. 63-80, including English Abstract on p. 64.

Magin, "Die belastungsstabile Lapidus-Arthrodese bei Hallux-valgus-Deformitt mittels IVP-Plattenfixateur (V-TEK- System)," Operative Orthopdie und Traumatologie, vol. 26, No. 2, 2014, pp. 184-195, including English Abstract on p. 186.

Merete Gmbh, "MetaFix OpenWedge," Retrieved from <http://www.merete-medical.com/de/produkte/fuss/hallux-valgus/metafixr-openwedge.html>, 2016, 4 pages (Google Translation).

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

Mizuno et al., "Detorsion Osteotomy of the First Metatarsal Bone in Hallux Valgus," Japanese Orthopaedic Association, Tokyo, 1956; 30:813-819.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect Of Ankle Flexion Angle On Axial Alignment Of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Myerson, "Cuneiform-Metatarsal Arthrodesis," The Foot and Ankle, Chapter 9, 1997, pp. 107-117.

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.

Michelangelo Bunion System, Surgical Technique, Instratek Incorporated, publication date unknown, 4 pages.

Tricot et al., "3D-corrective osteotomy using surgical guides for posttraumatic distal humeral deformity," Acta Orthopaedica Belgica, vol. 78, No. 4, 2012, pp. 538-542.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fuchirurgie Das V-tek-System," ABW Wissenschaftsverlag GmbH, 2009, 11 pages, including English Abstract.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Weber et al., "A Simple System For Navigation Of Bone Alignment Osteotomies Of The Tibia," International Congress Series, vol. 1268, Jan. 2004, pp. 608-613, (Abstract Only).

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Weil et al., "Anatomic Plantar Plate Repair Using the Weil Metatarsal Osteotomy Approach," Foot & Ankle Specialist, vol. 4, No. 3, 2011, pp. 145-150.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Wienke et al., "Bone Stimulation For Nonunions: What the Evidence Reveals," Podiatry Today, vol. 24, No. 9, Sep. 2011, pp. 52-57.

Wukich et al., "Hypermobility of the First Tarsometatarsal Joint," Foot and Ankle Clinics, vol. 10, No. 1, Mar. 2005, pp. 157-166.

(56)　　　　References Cited

OTHER PUBLICATIONS

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Couzens et al., "Stainless Steel Versus Titanium Volar Multi-Axial Locking Plates for Fixation of Distal Radius Fractures: A Randomised Clinical Trial," BMC Musculoskeletal Disorders, vol. 15, No. 74, Mar. 2014, 7 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
D'Amico et al., "Motion of the First Ray: Clarification Through Investigation," Journal of the American Podiatry Association, vol. 69, No. 1, Jan. 1979, pp. 17-23.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Dayton et al., "A new triplanar paradigm for bunion management," Lower Extremity Review, Apr. 2015, 9 pages.
Dayton et al., "A User-Friendly Method of Pin Site Management for External Fixators," Foot and Ankle Specialist, Sep. 16, 2011, 4 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Biwinged Excision for Round Pedal Lesions," The Journal of Foot and Ankle Surgery, vol. 35, No. 3, 1996, pp. 244-249.
Dayton et al., "Clarification of the Anatomic Definition of the Bunion Deformity," The Journal of Foot and Ankle Surgery, vol. 53, 2014, pp. 160-163.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the Literature," The Journal of Foot and Ankle Surgery, Article in Press, 2015, 3 pages.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Hallux Varus as Complication of Foot Compartment Syndrome," The Journal of Foot and Ankle Surgery, vol. 50, 2011, pp. 504-506.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "Medial Incision Approach to the First Metatarsophalangeal Joint," The Journal of Foot and Ankle Surgery, vol. 40, No. 6, November/Dec. 2001, pp. 414-417.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "The Extended Knee Hemilithotomy Position for Gastrocnemius Recession," The Journal of Foot and Ankle Surgery, vol. 49, 2010, pp. 214-216.
Dayton et al., "Use of the Z Osteotomy for Tailor Bunionectomy," The Journal of Foot and Ankle Surgery, vol. 42, No. 3, May/Jun. 2003, pp. 167-169.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Decarbo et al., "Locking Plates: Do They Prevent Complications?," Podiatry Today, Apr. 2014, 7 pages.
Decarbo et al., "Resurfacing Interpositional Arthroplasty for Degenerative Joint Disease of the First Metatarsalphalangeal Joint," Podiatry Management, Jan. 2013, pp. 137-142.
Decarbo et al., "The Weil Osteotomy: A Refresher," Techniques in Foot and Ankle Surgery, vol. 13, No. 4, Dec. 2014, pp. 191-198.
Defendant Fusion Orthopedics LLC's Invalidity Contentions, No. CV-22-00490-PHX-SRB, US District Court for the District of Arizona, Aug. 27, 2022, 41 pages.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

(56)                    References Cited

OTHER PUBLICATIONS

Easley et al., "Current Concepts Review: Hallux Valgus Part II: Operative Treatment," Foot and Ankle International, vol. 28, No. 6, Jun. 2007, pp. 748-758.
Easley et al., "What is the Best Treatment for Hallux Valgus?," Evidence-Based Orthopaedics—The Best Answers to Clinical Questions, Chapter 73, 2009, pp. 479-491.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Eustace et al., "Hallux valgus, first metatarsal pronation and collapse of the medial longitudinal arch—a radiological correlation," Skeletal Radiology, vol. 23, 1994, pp. 191-194.
Fallin et al., US Provisional Application Entitled Indexed Tri-Planar Osteotomy Guide and Method, U.S. Appl. No. 62/118,378, filed Feb. 19, 2015, 62 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Diaconu et al., "Locking Plates for Fixation of Extra-Articular Fractures of the First Metacarpal Base: A Series of 15 Cases, "Chirurgie de la Main, vol. 30, No. 1, pp. 26-30, Abstract only.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
"Futura Forefoot Implant Arthroplasty Products," Tornier, Inc., 2008, 14 pages.
"Hat-Trick Lesser Toe Repair System, Foot and Ankle Technique Guide, Metatarsal Shortening Osteotomy Surgical Technique," Smith & Nephew, 2014, 16 pages.
"Patient to Patient Precision, Accu-Cut, Osteotomy Guide System," BioPro, Foot & Ankle International Journal, vol. 23, No. 8, Aug. 2002, 2 pages.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
"Smith & Nephew scores a Hat-Trick with its entry into the high-growth hammer toe repair market," Smith & Nephew, Jul. 31, 2014, 2 pages.
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v =-jqJyE7pj-Y>, dated Nov. 2, 2009, 3 pages.
"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Acumed, "Acu-Loc Wrist Plating System," Brochure and Surgical Technique, effective date Apr. 2012, reported publication date Sep. 23, 2013, 19 pages.
Acumed, "Hand Fracture System," Brochure, effective date Sep. 2014, reported publication date Jan. 29, 2016, 6 pages.
Acumed, "Hub Cap Fusion Plates," Retrieved from <http://www.acumed.net/products/hand-wrist/carpal/hub-cap-fusion-plates>, 2016, 8 pages.
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Alvine et al., "Peg and Dowel Fusion of the Proximal Interphalangeal Joint," Foot & Ankle, vol. 1, No. 2, 1980, pp. 90-94.
Anderson et al., "Uncemented STAR Total Ankle Prostheses," The Journal of Bone and Joint Surgery, vol. 86(1, Suppl 2), Sep. 2004, pp. 103-111, (Abstract Only).
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Arthrex, "Double Compression Plates," Retrieved from <https://www.arthrex.com/foot-ankle/double-compression-plates>, 2016, 3 pages.
Arthrex, "Plantar Lapidus Plate," 2015, 6 pages.
Arthrex, "Proximal Metatarsal Osteotomy using Plates," Retrieved from <http://www.arthrex.com/foot-ankle/proximal-metatarsal-osteotomy-using-plates>, 2016, 2 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamrys Comprehensive Textbook of Foot and Ankle Surgery, Fourth Edition, vol. 1, Chapter 29, 2013, 26 pages.
Bednarz et al., "Modified Lapidus Procedure for the Treatment of Hypermobile Hallux Valgus," Foot & Ankle International, vol. 21, No. 10, Oct. 2000, pp. 816-821.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Catanese et al., "Measuring Sesamoid Position in Hallux Valgus: When Is the Sesamoid Axial View Necessary," Foot and Ankle Specialist, 2014, 3 pages.
Chang et al., "Lapidus Arthrodesis: A Different Perspective," Journal of the American Podiatric Medical Association, vol. 84, No. 6, Jun. 1994, pp. 281-288.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Coetzee et al., "Revision Hallux Valgus Correction," Operative Techniques in Foot and Ankle Surgery, Section I, Chapter 15, 2011, pp. 84-96.
Coetzee et al., "The Lapidus Procedure: A Prospective Cohort Outcome Study," Foot & Ankle International, vol. 25, No. 8, Aug. 2004, pp. 526-531.

(56) References Cited

OTHER PUBLICATIONS

Collan et al., "The biomechanics of the first metatarsal bone in hallux valgus: A preliminary study utilizing a weight bearing extremity CT," Foot and Ankle Surgery, vol. 19, 2013, pp. 155-161.

Conti et al., "Effect of the Modified Lapidus Procedure for Hallux Valgus on Foot Width," Foot & Ankle International, Feb. 1, 2020, published online: Oct. 30, 2019, 6 pages.

Conti et al., "Effect of the Modified Lapidus Procedure on Pronation of the First Ray in Hallux Valgus," Foot & Ankle International, Feb. 1, 2020, published online: Oct. 16, 2019, 8 pages.

Hat-Trick Lesser Toe Repair System, Smith & Nephew, Brochure, Aug. 2014, 12 pages.

Hoffmann II Compact External Fixation System, Stryker, Brochure, Literature No. 5075-1-500, 2006, 12 pages.

Hoffmann II Micro Lengthener, Stryker, Operative Technique, Literature No. 5075-2-002, 2008, 12 pages.

Hoffmann Small System External Fixator Orthopedic Instruments, Stryker, retrieved Dec. 19, 2014, from the Internet: <http://www.alibaba.com/product-detail/Stryker-Hoffmann-Small-System-External-Fixator_1438850129.html>, 3 pages.

Lag Screw Target Bow, Stryker Leibinger GmbH & Co. KG, Germany 2004, 8 pages.

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.

Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.

* cited by examiner

ANATOMICALLY-FITTED TARSOMETATARSAL BONE PLATE

CROSS-REFERENCE

This application claims the benefit of U.S. Provisional Patent Application No. 63/313,162, filed Feb. 23, 2022, the entire contents of which are incorporated herein by reference.

TECHNICAL FIELD

This disclosure generally relates to bone plate and, more particularly, to bone plate for use in fixating repositioned bones in the foot.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or realigning the first metatarsal relative to the adjacent metatarsal. In some procedures, a bone plate is used to fixate a position of the first metatarsal after realignment. The bone plate can be applied between the first metatarsal and medial cuneiform, across the tarsometatarsal joint. The bone plate can hold the first metatarsal in a realigned position while bone grows to form a fused connection between the first metatarsal and medial cuneiform.

SUMMARY

In general, this disclosure is directed to orthopedic bone plates as well as associated systems and surgical techniques utilizing such bone plates. In some implementations, the bone plate is used to fixate an anatomically corrected position of a bone following a realignment procedure. A bone plate as disclosed herein may be geometrically tailored to provide an anatomic fit complementary to the surface anatomy of one or more particular bones to which the bone plate is intended to be engaged.

In some examples, a bone plate as disclosed herein can be applied to a metatarsal bone and a cuneiform bone, for instance during a metatarsal fusion procedure. In one more specific example, the bone plate can be applied to a first metatarsal and a medial cuneiform separated by a first tarsometatarsal joint. The bone plate may be geometrically tailored to provide an anatomic fit complementary to the surface anatomy of the first metatarsal and/or the medial cuneiform. For instance, the bone plate may be contoured to anatomically fit the first metatarsal and the medial cuneiform. This can include configuring the bone plate to be angled in a first plane by a first plane angle to deviate away from a joint space between the medial cuneiform and the second cuneiform and/or to be angled in a second plane by a second plane angle to approximate a slope at a dorsal surface of the medial cuneiform. This can provide an anatomically-fitted bone plate for fixation the tarsometataral joint.

The anatomic fit provided by exemplary bone plates disclosed herein can facilitate robust plate fixation at the target bones, e.g., by reducing instances of inadequate fixation screw placement. For example, the anatomic fit provided by the bone plate may help prevent screw incursion into an adjacent joint space when installing the fixation plate (e.g., a joint space between the medial cuneiform and the second cuneiform) and/or help to avoid bone plate edge prominence at a cuneiform (e.g., at a slope at a dorsal surface of the medial cuneiform). This, in turn, may increase the robustness of the bone fixation provided by the bone plate while also avoiding unnecessary damage to adjacent ligaments and reducing the profile of the bone plate extending out from the bone surface.

For example, in practice, the proximal-lateral aspect of the medial cuneiform often exhibits a sharp slope or directional change where the medial cuneiform intersects the adjacent intermediate cuneiform (e.g., defining a C1-C2 joint space). If using a straight bone plate without anatomical contouring as described herein, the proximal-most fixation hole of the bone plate may be positioned at or over the proximal-lateral edge of the medial cuneiform when the bone plate is placed across the tarsometatarsal joint. When a fixation screw is subsequently inserted through the proximal-most fixation hole, the head of the screw may land in the C1-C2 joint space instead of the medial cuneiform. By configuring the bone plate to wrap along the contour of the medial cuneiform as described in some examples herein, the fixation holes of the bone plate may be appropriately positioned over the medial cuneiform to help avoid incursion into the C1-C2 joint space, improving fixation.

In one example, an anatomically-fitted bone plate for a metatarsal fusion procedure is described. This bone plate includes a body, a first fixation hole, a second fixation hole, a third fixation hole, and a fourth fixation hole. The body includes a proximal body region configured to be positioned over a cuneiform, a distal body region configured to be positioned over a metatarsal, and a bridge extending between the proximal body region and the distal body region that is configured to be positioned across a tarsometatarsal joint separating the metatarsal from the cuneiform. The bridge defines a bridge central longitudinal axis, the body has a width defining an extent of the bone plate transverse to the bridge central longitudinal axis, and the body includes a top surface and a bone facing surface opposite the top surface. The first fixation hole and the second fixation hole are located in the distal body region and positioned co-linear with the bridge central longitudinal axis. The first fixation hole and the second fixation hole each extend through the body from the top surface to the bone facing surface and are configured to receive a fixation screw therethrough. The third fixation hole and the fourth fixation hole are located in the proximal body region. The third fixation hole is positioned closer to the bridge than the fourth fixation hole. The third fixation hole is co-linear with the bridge central longitudinal axis, and the fourth fixation hole is offset from the bridge central longitudinal axis in a first plane by a first plane angle and in a second plane by a second plane angle. The third fixation hole and the fourth fixation hole each extend through the body from the top surface to the bone facing surface and are configured to receive the fixation screw therethrough.

In another example, a kit is described. The kit includes a first bone plate and a second bone plate. The first bone plate includes a body having four fixation holes, including a first fixation hole and a second fixation hole separated from a third fixation hole and a fourth fixation hole by a bridge. The first bone plate is configured to position the first fixation hole and the second fixation hole on a dorsal side of a metatarsal and the third fixation hole and the fourth fixation hole on the dorsal side of a cuneiform, with the bridge crossing the dorsal side of a tarsometatarsal joint space between the metatarsal and the cuneiform. The first, second, and third fixation holes are co-linearly aligned with the bridge and the fourth fixation hole is angled medially in a transverse plane and rotated plantarly on a frontal plane relative to first, second, and third fixation holes. The second bone plate includes a body having four fixation holes, including a first fixation hole and a second fixation hole separated from a third fixation hole and a fourth fixation hole by a bridge. The second bone plate is configured to position the first fixation hole and the second fixation hole on a medial side of the metatarsal and the third fixation hole and the fourth fixation hole on the medial side of the cuneiform, with the bridge crossing the medial side of the tarsometatarsal joint space between the metatarsal and the cuneiform. The first, second, and third fixation holes are co-linearly aligned with the bridge and the fourth fixation hole is angled dorsally in a sagittal plane and rotated laterally in the transverse plane relative to first, second, and third fixation holes.

In another example, a method of fixating a tarsometatarsal joint is described. The method includes positioning a bone plate over a portion of a metatarsal and over a portion of a cuneiform and across a tarsometatarsal joint separating the metatarsal from the cuneiform. Positioning the bone plate includes positioning a first fixation hole and a second fixation hole over the metatarsal and positioning a third fixation hole and a fourth fixation hole over the cuneiform with a bridge separating the second fixation hole from the third fixation hole extending across the tarsometatarsal joint. The first, second, and third fixation holes are arranged co-linearly with a bridge central longitudinal axis defined by the bridge and the fourth fixation hole is offset from the bridge central longitudinal axis in a first plane by a first plane angle and in a second plane by a second plane angle. And, the method includes inserting a fixation screw through each of the first fixation hole and the second fixation hole into the underlying metatarsal and through each of the third fixation hole and the fourth fixation hole into the underlying cuneiform.

The details of one or more examples are set forth in the accompanying drawings and the description below. Other features, objects, and advantages will be apparent from the description and drawings, and from the claims.

BRIEF DESCRIPTION OF DRAWINGS

FIGS. 1A and 1B are front views of a foot showing a normal first metatarsal position and an example frontal plane rotational misalignment position, respectively.

FIGS. 2A and 2B are top views of a foot showing a normal first metatarsal position and an example transverse plane misalignment position, respectively.

FIGS. 3A and 3B are side views of a foot showing a normal first metatarsal position and an example sagittal plane misalignment position, respectively.

FIGS. 4A-4D illustrate an embodiment of a bone plate. FIG. 4A is a top plan view of the bone plate, FIG. 4B is a proximal end elevational view of the bone plate, FIG. 4C is a side elevational view of the bone plate, and FIG. 4D is bottom plan view of the bone plate.

FIG. 5 is a top plan view of an embodiment of a kit.

FIG. 6 is a flow diagram of an embodiment of a surgical technique that includes positioning and fixating bone plates.

FIGS. 7A-7C illustrate an embodiment of first and second bone plates positioned and fixated at metatarsal and cuneiform bones and across a tarsometatarsal joint. FIG. 7A is a top plan view of the positioned and fixated bone plates, FIG. 7B is an end elevational view of the positioned and fixated bone plates, and FIG. 7C is a side elevational view of the positioned and fixated bone plates.

FIGS. 8A-8C illustrate another embodiment of a bone plate. FIG. 8A is a perspective view of the bone plate, FIG. 8B is a side elevational view of the bone plate including fixation screws, and FIG. 8C is an end elevational view of the bone plate including fixation screws.

FIGS. 9A-9C illustrate an additional embodiment of a bone plate. FIG. 9A is an end (e.g., proximal end) elevational view of the bone plate with fixation screws, FIG. 9B is side elevational view of the bone plate with fixation screws, and FIG. 9C is a top plan view of the bone plate with fixation screws.

Like reference characters are used in the following description and in the drawings to indicate like elements.

DETAILED DESCRIPTION

This disclosure generally relates to bone plates and associated systems (e.g., kits) and techniques incorporating one or more such bone plates. In some examples, a bone plate according to the disclosure can be used to fixating a repositioned bone during a surgical procedure, such as a metatarsal realignment and fusion procedure. In exemplary applications, the devices, systems, and techniques can be used during a surgical procedure performed on one or more bones, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing devices and/or techniques of the disclosure can be performed to correct an alignment between a metatarsal (e.g. a first metatarsal) and a cuneiform (e.g., a medial cuneiform), such as a bunion correction. An example of such a procedure is a lapidus procedure. In another example, the devices, systems, and/or techniques can be utilized when modifying a position of one portion of a bone relative to another portion of the same bone. An example of such a procedure is an osteotomy procedure (e.g., metatarsal osteotomy procedure) in which the bone is cut into at least two different bones and one portion (e.g., a distal portion) is realigned relative to another bone portion (e.g., a proximal portion) of the same bone.

Preparation and fusion of two opposed bone portions, such as a metatarsal and cuneiform, may be performed according to the disclosure for a variety of clinical reasons and indications. Preparation and fusion of a metatarsal and cuneiform at the tarsometatarsal ("TMT") joint may be performed to treat hallux valgus and/or other bone and/or joint conditions.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux abductus angle, the angle between the long axes of the first metatarsal and proximal phalanx in the transverse plane. An increase in the hallux abductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced (e.g., laterally relative to the first metatarsophalangeal joint), resulting in subluxation of the joints between the sesamoid bones and the head of the first metatarsal. This can increase the pressure between the medial sesamoid and the crista of the first metatarsal head.

While techniques and devices are generally described herein in connection with the first metatarsal and medial cuneiform of the foot, the techniques and devices may be used on other adjacent bones (e.g., separated from each other by a joint) and/or adjacent bone portions (e.g., portions of the same bone separated from each other by a fracture or osteotomy). In various examples, the devices, systems, and/or techniques of the disclosure may be utilized on comparatively small bones in the foot such as a metatarsal (e.g., first, second, third, fourth, or fifth metatarsal), a cuneiform (e.g., medial, intermediate, lateral), a cuboid, a phalanx (e.g., proximal, intermediate, distal), and/or combinations thereof. The bones may be separated from each other by a tarsometatarsal ("TMT") joint, a metatarsophalangeal ("MTP") joint, or other joint. Accordingly, reference to a first metatarsal and medial cuneiform herein may be replaced with other bone pairs as described herein. Further, where a bone plate according to the disclosure is intended to be used on a different bone or combination of bones other than the first metatarsal and medial cuneiform, the configuration of the bone plate (e.g., size, shape) may be adjusted to accommodate the specific bone or combination of bones being plated while following the bone plate configuration teachings outlined herein.

To further understand example devices and techniques of the disclosure, the anatomy of the foot will first be described with respect to FIGS. 1-3 along with example misalignments that may occur and be corrected and fixated according to the present disclosure. A bone misalignment may be caused by hallux valgus (bunion), a natural growth deformity, and/or other condition.

Figure 1A:
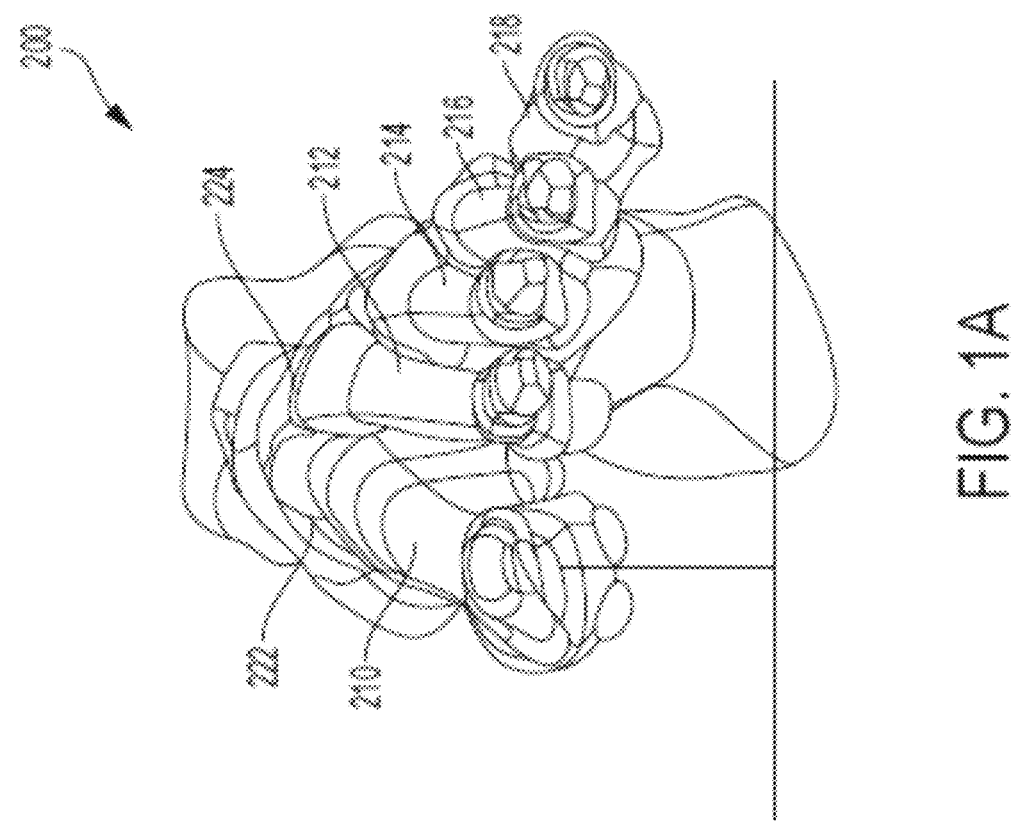
Figure 2B:
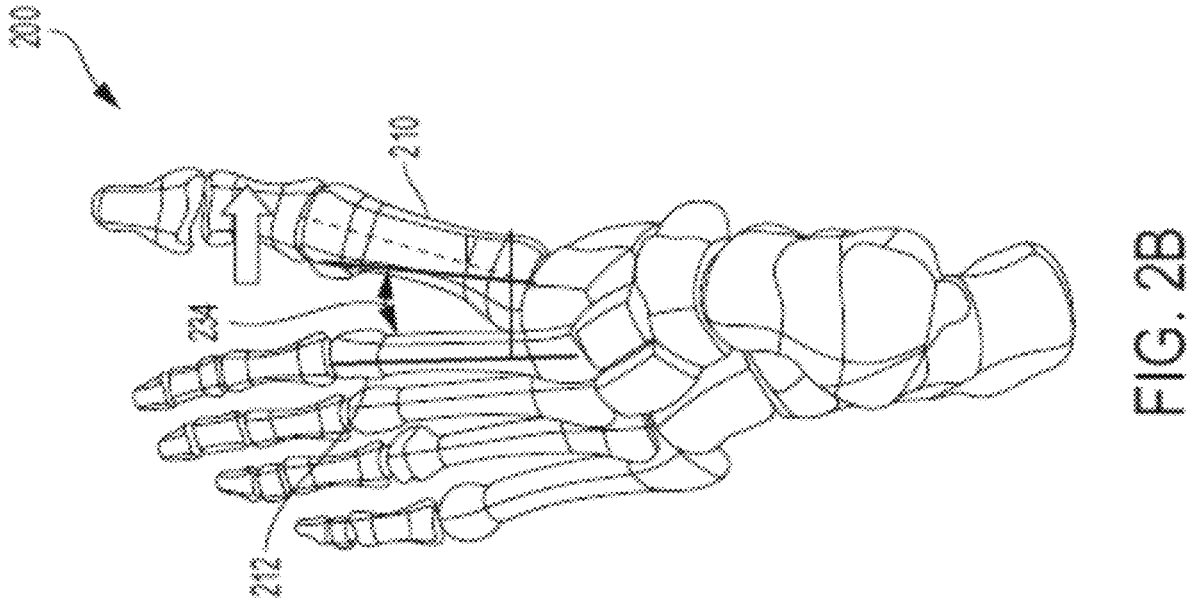
Figure 2A:
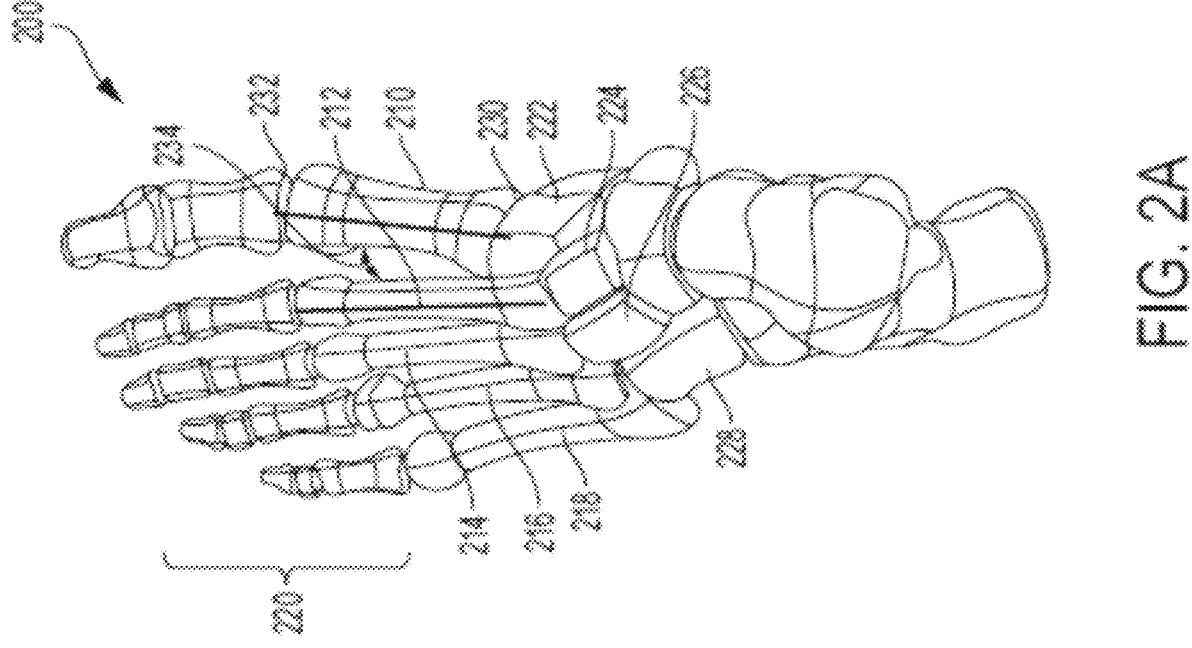
Figures 3A, 3B:
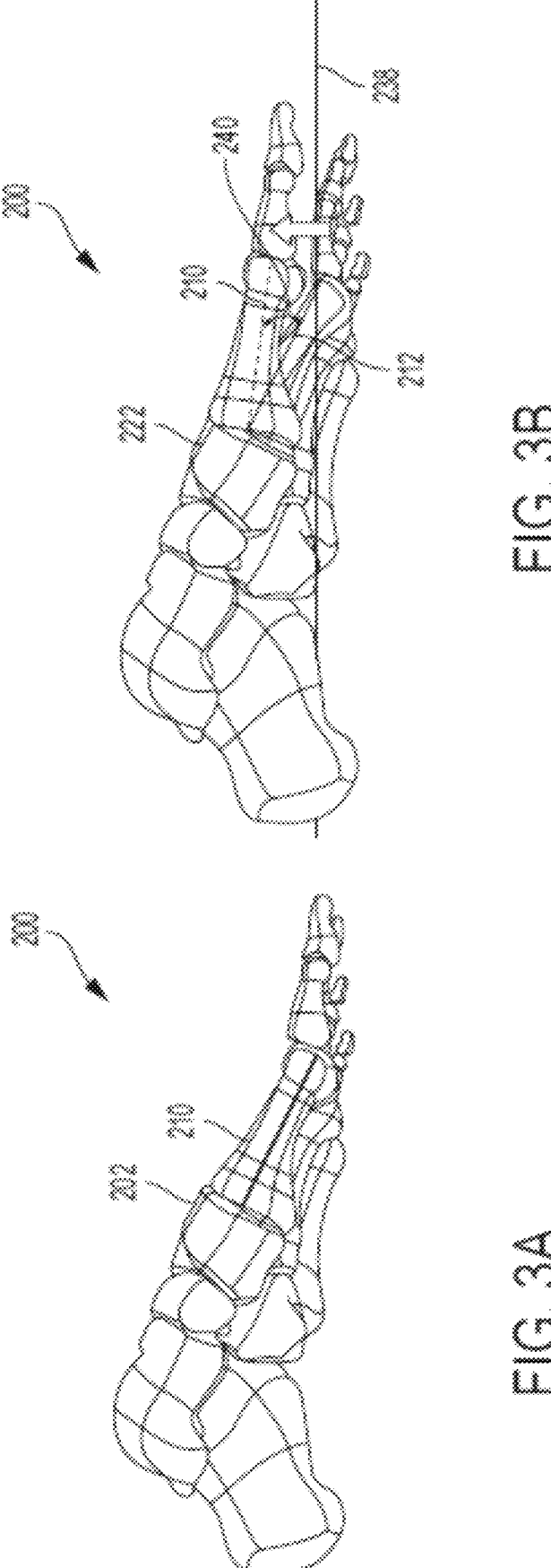

FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected. Further, a bone condition treated according to the disclosure may not present any of the example misalignments described with respect to FIGS. 1B, 2B, and 3B, and it should be appreciated that the disclosure is not limited in this respect.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal 214 is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

Surgical techniques and instruments according to the disclosure can be useful during a procedure to correct a misalignment of one or more bones, such as the metatarsal and opposed cuneiform, and/or promote fusion of the metatarsal and cuneiform across the TMT joint. In some applications, a realignment procedure involves surgically accessing the TMT joint (e.g., from a medial side of the foot and/or a dorsal side of the foot). The clinician can insert a bone preparation instrument through an incision to prepare the end face of one or both bones.

Before or after preparing one or both ends of first metatarsal 210 and medial cuneiform 222, the clinician can realign the metatarsal relative to the cuneiform. The clinician can pivot the distal end of first metatarsal 210 laterally toward second metatarsal 212 to close an intermetatarsal angle between the first and second metatarsal. Additionally or alternatively, the clinician can rotate first metatarsal 210 in the frontal plane to correct a frontal plane rotation of the metatarsal and/or move the first metatarsal 210 in the sagittal plane to correct a sagittal plane position of the metatarsal. Realignment of first metatarsal 210 can be performed free-hand by the clinician or with the aid of a bone positioning device to facilitate the realignment. After desired realignment in one or more planes, the clinician can fixate the moved position first metatarsal 210 by applying one or more fixation devices (e.g., one or more pins, plates, screws, staples, rods), at least one of which may be a bone plate as configured herein.

Figure 4A:
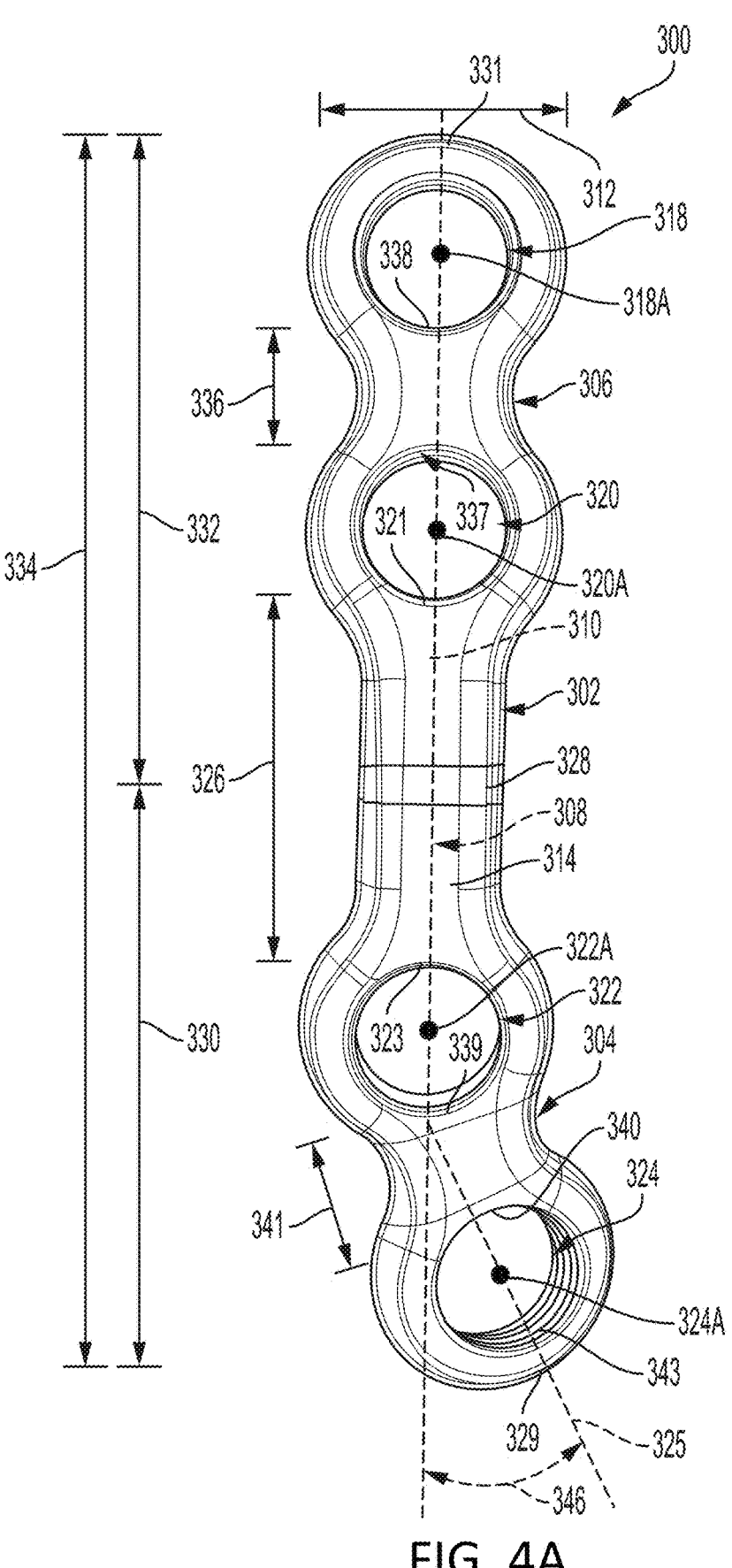
Figure 4B:
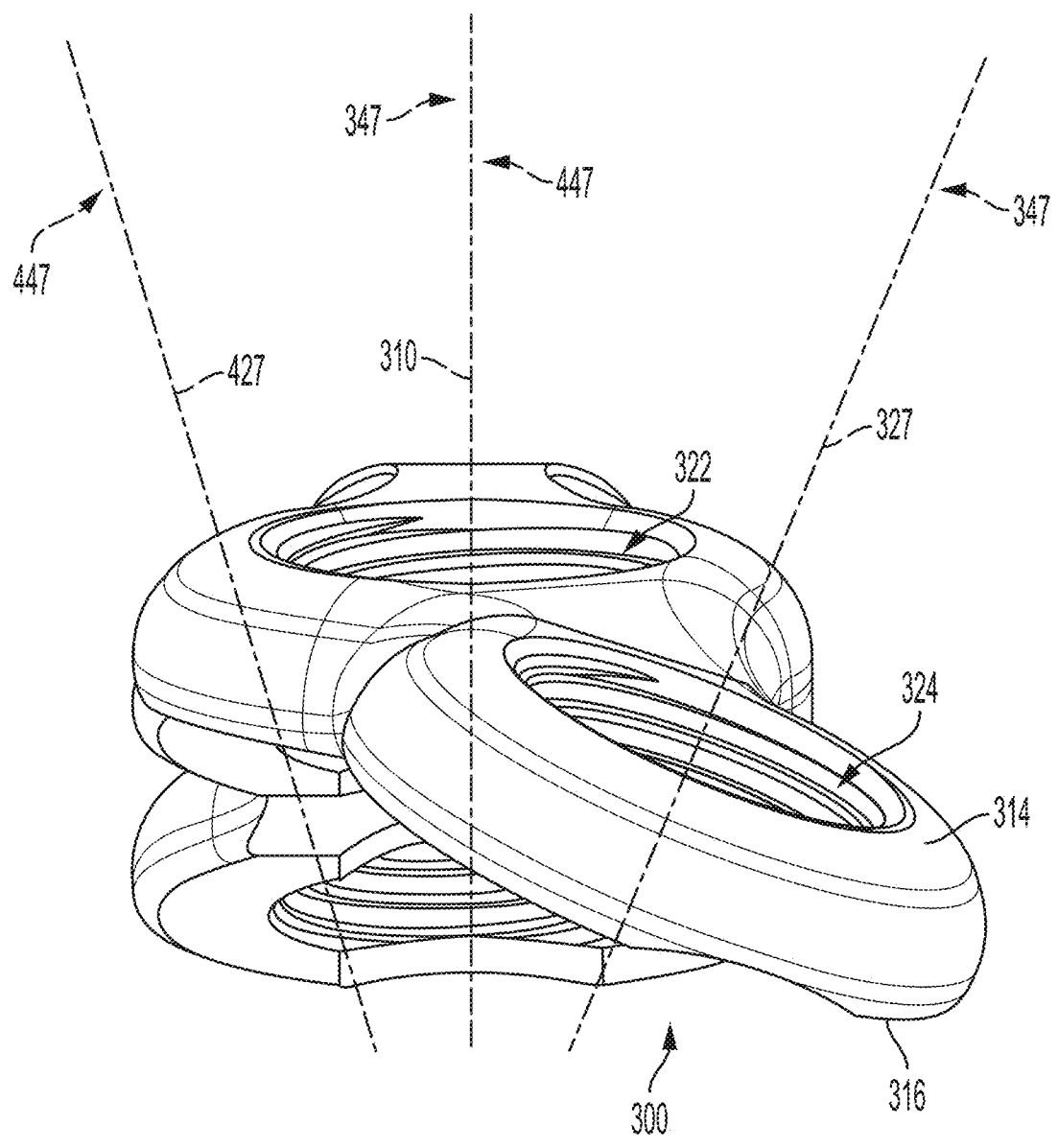
Figure 4C:
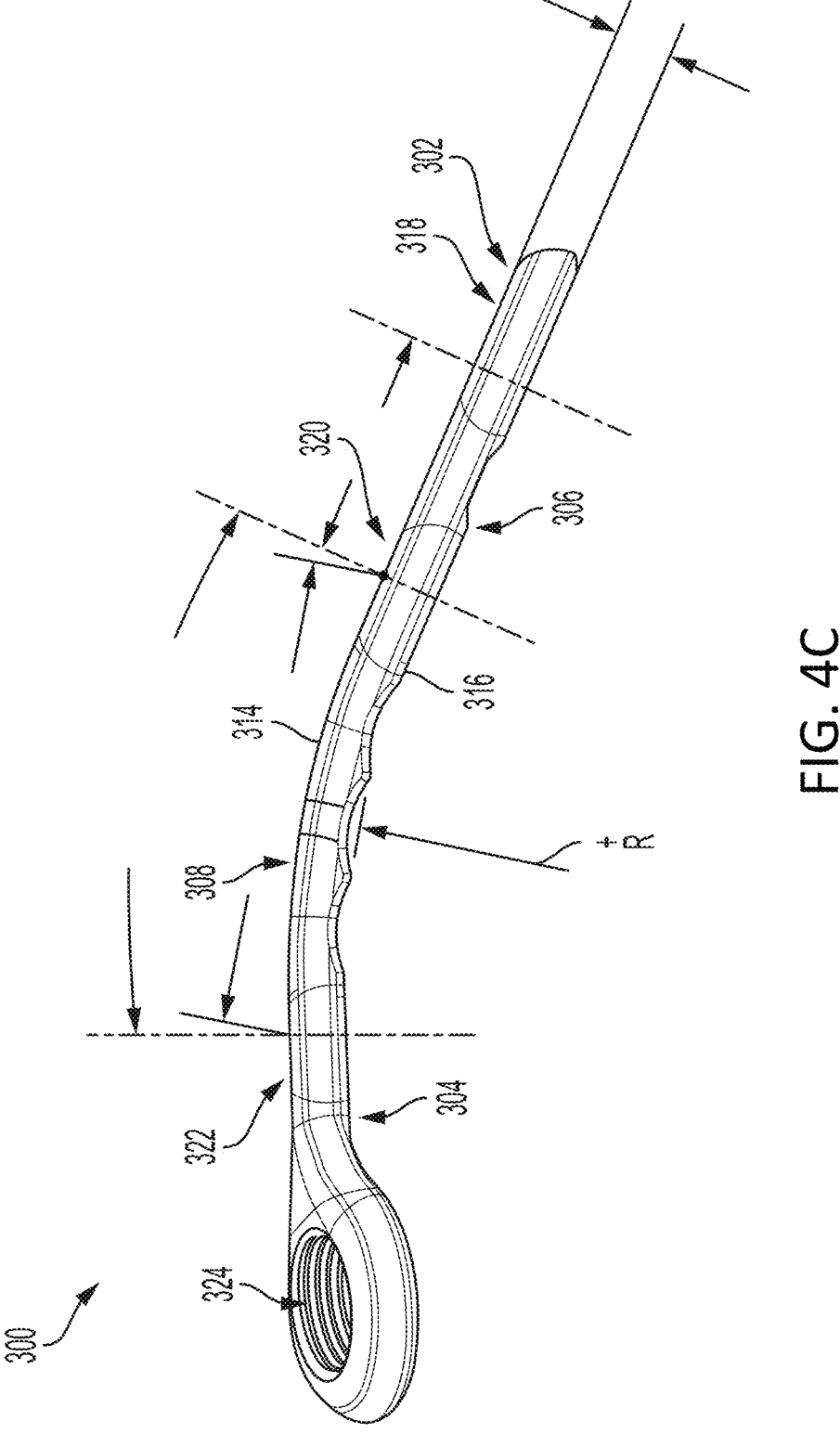
Figure 4D:
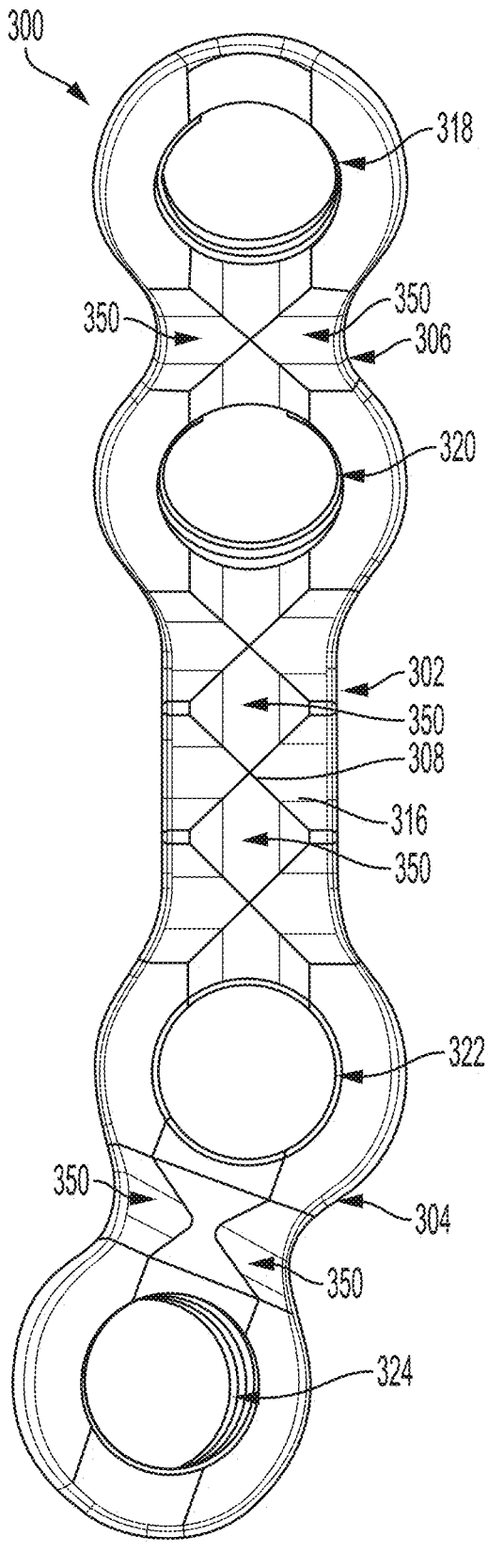

FIGS. 4A, 4B, 4C, and 4D (collectively referred to as "FIG. 4") are different view of an embodiment of a bone plate 300 that can be used to fixate bones, such as a metatarsal bone and a cuneiform bone across the tarsometatarsal joint during a bone realignment procedure, such as a metatarsal realignment procedure. As will be described elsewhere herein, bone plate 300 can be an anatomically-fitted bone plate that is geometrically configured to fit the anatomical shape of one or more particular bones. As one example, bone plate 300 can be anatomically fitted for a metatarsal fusion procedure such that bone plate 300 includes one or more geometric features that are complementary to the anatomical shape of a cuneiform (e.g., medial cuneiform) and/or metatarsal (e.g., first metatarsal). FIG. 4A is a top plan view of bone plate 300, FIG. 4B is a proximal end elevational view of bone plate 300, FIG. 4C is a side elevational view of the bone plate 300, and FIG. 4D is bottom plan view of the bone plate 300.

As shown at FIG. 4, bone plate 300 can include a body 302. Body 302 can include a proximal body region 304, a distal body region 306, and a bridge 308. Proximal body region 304 can be configured to be positioned over a cuneiform, such as a medial cuneiform. Distal body region 306 can be configured to be positioned over a metatarsal, such as a first metatarsal. Bridge 308 can extend between proximal body region 304 and distal body region 308. Bridge 308 can be configured to be positioned across a tarsometatarsal joint separating the metatarsal from the cuneiform. Bridge 308 can define a bridge central longitudinal axis 310. Body 302 can have a width 312 defining an extent of bone plate 300 transverse to bridge central longitudinal axis 310. In addition, body 302 can include a top surface 314 and a bone facing surface 316 that is opposite top surface 314.

Bone plate 300 can also include fixation holes. In general, body 302 may include at least one fixation hole extending through the proximal body region 304 and at least one fixation hole extending through the distal body region 306. In different examples, body may include more fixation hole extending through the proximal body region 304 (e.g., two or more) and/or more fixation hole extending through the distal body region 306 (e.g., two, three, or more).

As shown at FIG. 4, bone plate 300 includes a first fixation hole 318, a second fixation hole 320, a third fixation hole 322, and a fourth fixation hole 324. First fixation hole 318 and second fixation hole 320 can be located in the distal body region 306, and first fixation hole 318 and second fixation hole 320 can each extend through body 302 from top surface 314 to bone facing surface 316. As also shown for the illustrated embodiment, second fixation hole 320 is positioned closer to bridge 308 than first fixation hole 318. Third fixation hole 322 and fourth fixation hole 324 can be located in the proximal body region 304, and third fixation hole 322 and fourth fixation hole 324 can each extend through body 302 from top surface 314 to bone facing surface 316. As shown in the illustrated embodiment, third fixation hole 322 is positioned closer to bridge 308 than fourth fixation hole 324. Each of first fixation hole 318, second fixation hole 320, third fixation hole 322, and fourth fixation hole 324 can be configured to receive a fixation screw therethrough.

For the illustrated bone plate 300, the first fixation hole 318, second fixation hole 320, third fixation hole 322, and fourth fixation hole 324 are the only fixation holes provided by bone plate 300. In other words, bone plate 300 has only two fixation holes on the proximal bone plate and only two fixation holes on the distal bone plate portion. In other bone plate embodiments, other numbers of fixation holes can be utilized.

As noted, bone plate 300 can include one or more features to anatomically fit the plate to one or more bones over which bone plate 300 is to be positioned and fixated. As one example, bridge 308 can be configured to be positioned across a tarsometatarsal joint that separates a metatarsal and a cuneiform. Bridge 308 can have a length 326 extending from an edge 321 of second fixation hole 320 to an edge 323 of third fixation hole 322. Length 326 of bridge 308 can range from 5.0 mm to 15.0 mm, such as ranging from 5.5 mm to 14.5 mm, from 6.0 mm to 14.25 mm, from 6.0 mm to 11.0 mm, or from 9.0 mm to 11.0 mm. Length 326 of bridge 308 can have a midline 328 halfway between edge 321 of second fixation hole 320 and edge 323 of third fixation hole 322. As another example, body 302 can define a proximal length 330 extending from midline 328 of bridge 308 to a proximal edge 329 of bone plate 300, for instance, to position proximal body region 304 over a metatarsal (e.g., a first metatarsal). Proximal length 330 can range from 8-20 mm, such as from 12-20 mm or from 17-20 mm, and proximal length 330 can be less than 18.5 mm, such as less than 18.0 mm or less than 15.0 mm. Similarly, body 302 can define a distal length 332 extending from midline 328 of bridge 308 to a distal edge 331 of bone plate 300, for instance, to position distal body region 306 over a cuneiform (e.g., a medial cuneiform). Distal length 332 can range from 8-20 mm, such as from 12-20 mm or from 15-18 mm. In some cases, distal length 332 can be greater than proximal length 330 such that a ratio of distal length 332 divided by proximal length 330 can be greater than 1.0, such as greater than 1.03, greater than 1.1, greater than 1.15, greater than 1.2, or greater than 1.25. And, body 302 can define an overall length 334 from proximal edge 329 to distal edge 331 ranging from 16-50 mm, such as from 24-46 mm or from 30-40 mm.

To further facilitate an anatomical fit and fixation of bone plate 300 at one or more bones, bone plate 300 can include one or more intra-hole spacings to facilitate suitable fixation screw placement at a target bone. For example, a distance between first fixation hole 318 (e.g., a proximal edge 338 of first fixation hole 318 closest to second fixation hole 320) and second fixation hole 320 (e.g., a distal edge 337 of second fixation hole 320 closest to first fixation hole 318) can define a first intra-hole spacing 336. First intra-hole spacing 336 can range from 2-12 mm, such as from 5-10 mm, from 7-9 mm, or 3.25-4.50 mm, and a ratio of first intra-hole spacing 336 to the length 326 of bridge 308 can be at least 0.78. This first intra-hole spacing 336 can be configured to place each of first fixation hole 318 and second fixation hole 320 over the metatarsal (e.g., first metatarsal). As another example, a distance between third fixation hole 322 (e.g., a proximal edge 339 of third fixation hole 322 closest to fourth fixation hole 324) and fourth fixation hole 324 (e.g., a distal edge 340 of fourth fixation hole 324 closest to third fixation hole 322) can define a second intra-hole spacing 341. Second intra-hole spacing 341 can range from 2-12 mm, such as 5-10 mm or 7-9 mm, and a ratio of second intra-hole spacing 341 to the length of the bridge is at least 0.78. This second intra-hole spacing 341 can be configured, in some applications with one or more other anatomical fit features at the proximal body region 304 described later herein, to place each of third fixation hole 322 and fourth fixation hole 324 over the cuneiform (e.g., medial cuneiform).

In addition, width 312 of body 302 can be configured to help facilitate an anatomical fit and fixation of bone plate 300 at one or more bones. For example, width 312 of body 302 can be greater at locations of body 302 defining each of first fixation hole 318, second fixation hole 320, third fixation hole 322, and fourth fixation hole 324 than width 312 of body 302 is at bridge 308. As another example, width 312 of body 302 can be less at locations longitudinally between first fixation hole 318, second fixation hole 320, third fixation hole 322, and fourth fixation hole 324 than width 312 of body 302 at locations of body 302 defining first fixation hole 318, second fixation hole 320, third fixation hole 322, and fourth fixation hole 324. These widths 312 of the body 302 can provide an efficient profile of the bone plate 302 for placement at relatively small bones, such as the metatarsal and cuneiform in the foot, while yet still providing fixation points at bone plate 300 for robust fixation of bone plate 300 to these relatively smaller bones.

Body 302 of bone plate 300 can be flat or can include an arched profile along its length. For example, as best seen at FIG. 4C, body 302 can be arched along at least a portion of overall length 334 with bone facing surface 316 defining a concave profile and top surface 314 defining a convex profile. For example, body 302 can be arched with an apex of the arched profile generally at the center of bridge 308, a low point at distal body region 306 generally at first fixation hole 318, and a low point at proximal body region 304 generally at fourth fixation hole 324. Body 302 can define the arch profile with a center radius R (e.g., at the center of bridge 308) ranging from 20.0 mm to 25.0 mm, such as from 21.0 mm to 24.0 mm, from or 22.0 mm to 23.0 mm.

To further help facilitate an anatomical fit of bone plate 300 to one or more bones, body 302 can define bone plate 300 as an asymmetric bone plate. In particular, bone plate 300 can be contoured to complement the target anatomy of the one or more bones and/or adjacent joint space(s) over which bone plate 300 is to be positioned and fixated. To complement the target anatomy, bone plate 300 can include fourth fixation hole 324 in an asymmetric orientation relative to one or more other fixation holes (e.g., relative to each of first fixation hole 318, second fixation hole 320, and third fixation hole 322). In particular, bone plate 300 can include fourth fixation hole 324 in this asymmetric orientation such that fourth fixation hole 324 complements the native anatomy present at a cuneiform (e.g., present at the medial cuneiform) and/or the joint space between adjacent the cuneiform (e.g., the joint space adjacent the medial cuneiform and the intermediate cuneiform). Thus, the asymmetric orientation of fourth fixation hole 324 can help to provide bone plate 300 as an anatomically-fitted bone plate that complements the native anatomy present at the cuneiform in way that helps to avoid inadvertent fixation screw placement at a joint space and positions fourth fixation hole 324 in a manner that accounts for the native anatomy at the cuneiform to facilitate robust fixation screw securement at that native anatomy.

As seen for bone plate 300 at FIG. 4, fourth fixation hole 324 can be offset from bridge central longitudinal axis 310 while first fixation hole 318, second fixation hole 320, and third fixation hole 322 are located on bridge central longitudinal axis 310. More specifically, in some examples, as seen best at FIG. 4A, each of first fixation hole 318, second fixation hole 320, and third fixation hole 322 can be positioned co-linear with bridge central longitudinal axis 310 while fourth fixation hole 324 is offset from bridge central longitudinal axis 310 in more than one plane. As one such example, first fixation hole 318 can have a geometric center 318A, second fixation hole 320 can have a geometric center 320A, third fixation hole 322 can have a geometric center 322A, and fourth fixation hole 324 can have a geometric center 324A. The geometric center 324A of fourth fixation hole 324 is offset from bridge central longitudinal axis 310 while each of geometric center 318A of first fixation hole 318, geometric center 320A of second fixation hole 320, and geometric center 322A of third fixation hole 322 is positioned substantially along bridge central longitudinal axis 310.

Geometric centers 318A, 320A, and 322A being positioned substantially along bridge central longitudinal axis 310 can include geometric centers 318A, 320A, and 322A being bisected by bridge central longitudinal axis 310. Alternately, geometric centers 318A, 320A, and 322A being positioned substantially along bridge central longitudinal axis 310 can include geometric centers 318A, 320A, and 322A more generally intersecting bridge central longitudinal axis 310 at some portion of geometric centers 318A, 320A, and 322A although geometric centers 318A, 320A, and 322A need not necessarily be strictly aligned with one another. For instance, geometric centers 318A, 320A, and 322A can each intersect bridge central longitudinal axis 310 at some portion of geometric centers 318A, 320A, and 322A while a true center of one or more of geometric centers 318A, 320A, and 322A is within 2%, 5%, 7%, 10%, 12%, 15%, 17%, 20%, 25%, 30%, 35%, or 40% of bridge central longitudinal axis 310.

As noted, fourth fixation hole 324 can be offset from bridge central longitudinal axis 310 in more than one plane. More specifically, fourth fixation hole 324 can be offset from bridge central longitudinal axis 310 in a first plane by a first plane angle and in a second plane by a second plane angle. For example, geometric center 324A of fourth fixation hole 324 can be offset from bridge central longitudinal axis 310 in the first plane by a distance ranging from 0.25-10.0 mm, such as from 0.5-7.0 mm or from 1.0-4.0 mm. As another example, geometric center 324A of fourth fixation hole 324 can be offset from bridge central longitudinal axis 310 in the second plane at an angle ranging from 1° to 50°, from 5° to 40°, or from 15° to 30°.

As to the offset orientation of fourth fixation hole 324 in the first plane by the first angle, for example, a portion of proximal body region 304 defining fourth fixation hole 324 can include a bend of body 302 deviating from bridge central longitudinal axis 310 in the first plane by a first plane angle 346. More specifically, as best seen at FIG. 4A, fourth fixation hole 324 can define a first fourth fixation hole axis 325 along which fourth fixation hole 324 extends generally between distal edge 340 of fourth fixation hole 324 and proximal edge 343 of fourth fixation hole 324. And, the portion of proximal body region 304 can include the bend of body 302 in an orientation that deviates first fourth fixation hole axis 325 from bridge central longitudinal axis 310 in the first plane by first plane angle 346. In specific applications of bone plate 300 at one or more bones in the foot, the first plane can be, for instance, the transverse plane, and the bend of body 302 can deviate first fourth fixation hole axis 325 from bridge central longitudinal axis 310 in the first plane by first plane angle 346 in a medial direction. In another instance where bone plate 300 is applied at one or more bones in the foot, the first plane can be, for instance, the sagittal plane, and the bend of body 302 can deviate from bridge central longitudinal axis 310 in the first plane by first plane angle 346 in a dorsal direction. As examples, first plane angle 346 can range from 1° to 50°, from 5° to 40°, or from 15° to 30°. Such ranges for first plane angle 346, and particularly 5° to 40° or 15° to 30°, can be useful in orienting fourth fixation hole 324 (e.g., in the first plane) in a manner that accounts for native anatomy at the cuneiform bone since the bend defined by first plane angle 346 can be helpful in angling fourth fixation hole 324 away from a joint space adjacent the cuneiform and/or angling fourth fixation hole 324 toward a stable fixation surface at the cuneiform.

As to the offset orientation of fourth fixation hole 324 in the second plane by the second angle, for example, a portion of proximal body region 304 defining fourth fixation hole 324 can include a twist of body 302 deviating from bridge central longitudinal axis 310 in the second plane by a second plane angle 347. More specifically, as best seen at FIG. 4B, fourth fixation hole 324 can define a second fourth fixation hole axis 327 along which fourth fixation hole 324 extends through body 302 from top surface 314 to bone facing surface 316. And, the portion of proximal body region 304 can include the twist of body 302 in an orientation that deviates second fourth fixation hole axis 327 from bridge central longitudinal axis 310 in the second plane by second plane angle 347.

In specific applications of bone plate 300 at one or more bones in the foot, the second plane can be, for instance, the frontal plane, and the twist of body 302 can deviate second fourth fixation hole axis 327 from bridge central longitudinal axis 310 in the second plane by second plane angle 347 in a plantar direction. In another instance where bone plate 300 is applied at one or more bones in the foot, the second plane can be, for instance, the transverse plane, and the twist of body 302 can deviate from bridge central longitudinal axis 310 in the second plane by second plane angle 347 in a lateral direction. As examples, second plane angle 347 can range from 1° to 50°, from 5° to 40°, or from 15° to 30°. Such ranges for second plane angle 347, and particularly 5° to 40° or 15° to 30°, can be useful in orienting fourth fixation hole 324 (e.g., in the second plane) in a manner that accounts for native anatomy, such as contouring, at the cuneiform bone since the twist defined by second plane angle 347 can be helpful in rotating fourth fixation hole 324 to an orientation that complements the surface geometry at the cuneiform to facilitate a stable, more flush contact between bone facing surface 316 at the portion of proximal body region 304 having fourth fixation hole 324 and the underlying surface of the cuneiform.

In some examples, as best seen at FIG. 4D, to further help fit bone plate 300 to the anatomy of one or more target bones, bone plate 300 can include one or more recessed regions 350. The one or more recessed regions 350 can be configured to facilitate contouring of bone plate 300. As such, the one or more recessed regions 350 can be configured to facilitate additional bending and/or twisting of bone plate 300, at regions of bone plate 300 where a recessed region 350 is present, as desired by a clinician prior to placement of bone plate 300. When included, the one or more recessed regions 350 can be located at bone facing surface 316. In use, for example, the clinician may insert plate benders into different holes of body 300 and bend the plate along its longitudinal axis to conform the plate to the anatomy of a specific patient undergoing a surgical procedure.

As illustrated at FIG. 4D, bone plate 300 can include at least one recessed region 350 located longitudinally between third fixation hole 322 and fourth fixation hole 324 at bone facing surface 316. Moreover, because the at least one recessed region 350 can be located longitudinally between third fixation hole 322 and fourth fixation hole 324, this at least one recessed region 350 can also likewise be located at the portion of the proximal body region 304 that is offset from the bridge central longitudinal axis 310. Thus, because the at least one recessed region 350 can be located longitudinally between third fixation hole 322 and fourth fixation hole 324, this at least one recessed region 350 can be located at a portion of body 302 that includes a bend and a twist of body 302 deviating fourth fixation hole 324 from bridge central longitudinal axis 310. In one specific example, longitudinally between third fixation hole 322 and fourth fixation hole 324, bone facing surface 316 can include one recessed region 350 extending radially inward from a first lateral side of body 302 and another recessed region 350 extending radially inward from a second, opposite lateral side of body 302 with an elevated region located radially between these two radially inward extending recessed regions 350.

To facilitate certain surgical procedures, a kit can be provided with one or more bones plates disclosed herein. Such a kit can be useful, for example, in fixating repositioned bones during a surgical procedure, such as a metatarsal realignment and fusion procedure.

Figure 5:
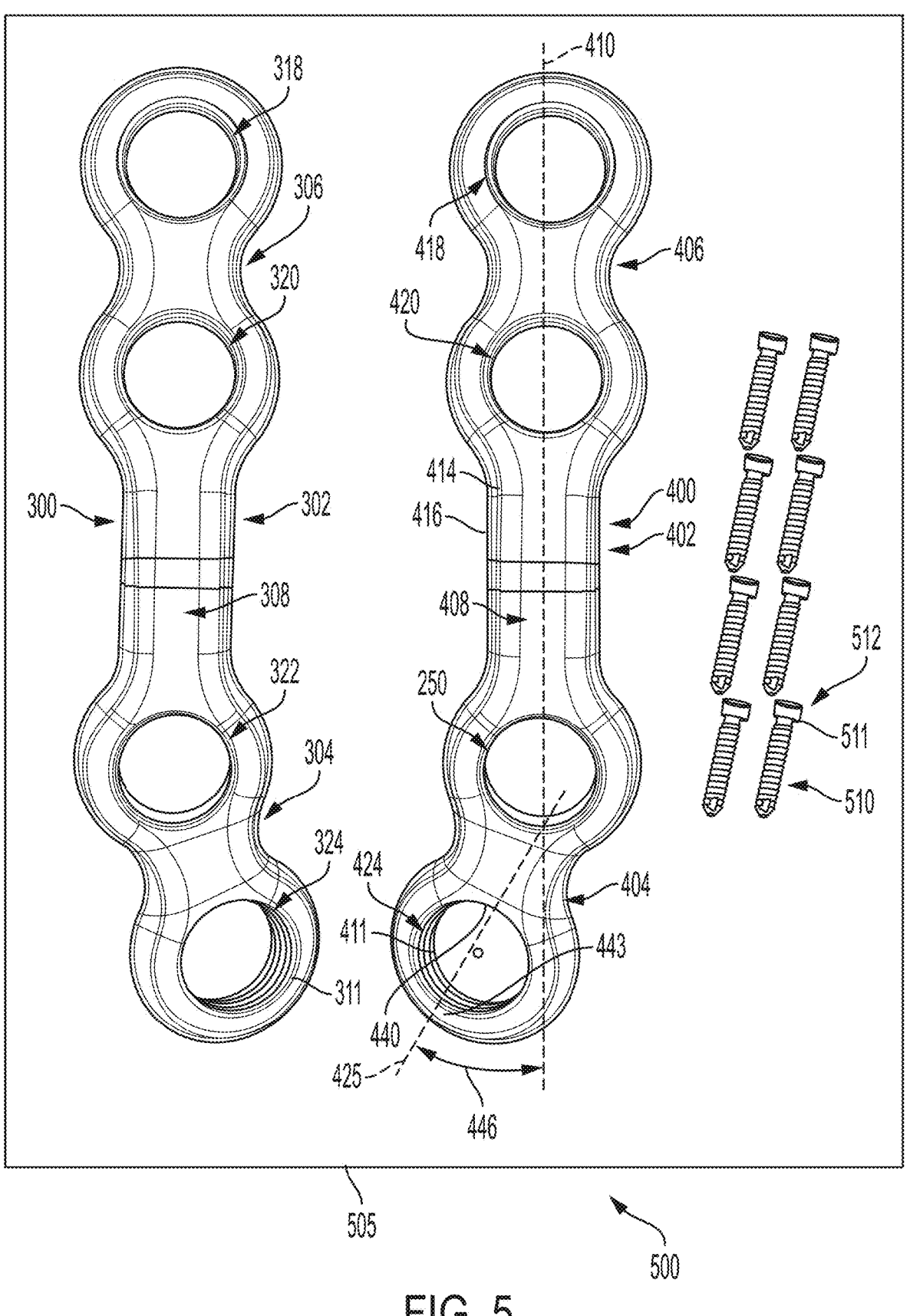

FIG. 5 is a top plan view of an embodiment of a kit 500. Kit 500 can include a first bone plate, such as bone plate 300, and a second bone plate 400. Kit 500 can also include a sterile container 505, with bone plate 300 and bone plate 400 in the sterile container 505. In addition, as shown for the embodiment at FIG. 5, kit 500 can additionally include one or more fixation screws 510 in the sterile container 505 with bone plate 300 and bone plate 400. In general, the number of fixation screws in the kit may be equal to or greater than the number of fixation holes provide by the bone plate to be used during the surgical procedure (e.g., the number of fixation holes provide by multiple bone plate when multiple plates are to be used during the surgical procedure). In one specific example, kit 500 can include at least four fixation screws 510 in the sterile container 505, such as exactly four, at least eight, exactly eight, or yet other numbers of fixation screws. The components within sterile container 505 can be sealed within sterile container 505 so as to preserve a sterilized state of these components while in the sterile container 505.

Bone plate 400 can be similar to, or the same as, that disclosed elsewhere herein with respect to bone plate 300 except as noted here. Namely, bone plate 400 can be similar to, or the same as, bone plate 300 except that bone plate 400 can differ from bone plate 300 in that bone plate 400 includes a fourth fixation hole 424 offset from a bridge central longitudinal axis 410 in a different orientation than fourth fixation hole 324 is offset from bridge central longitudinal axis 310. For example, fourth fixation hole 424 of bone plate 400 can be offset from bridge central longitudinal axis 410 in an orientation that is a mirror image of the orientation at which fourth fixation hole 324 of bone plate 300 is offset from bridge central longitudinal axis 310. Including such bone plate 300 and bone plate 400 can facilitate surgical procedures, such as a metatarsal realign-

US 12,697,154 B2

Figure 7A:
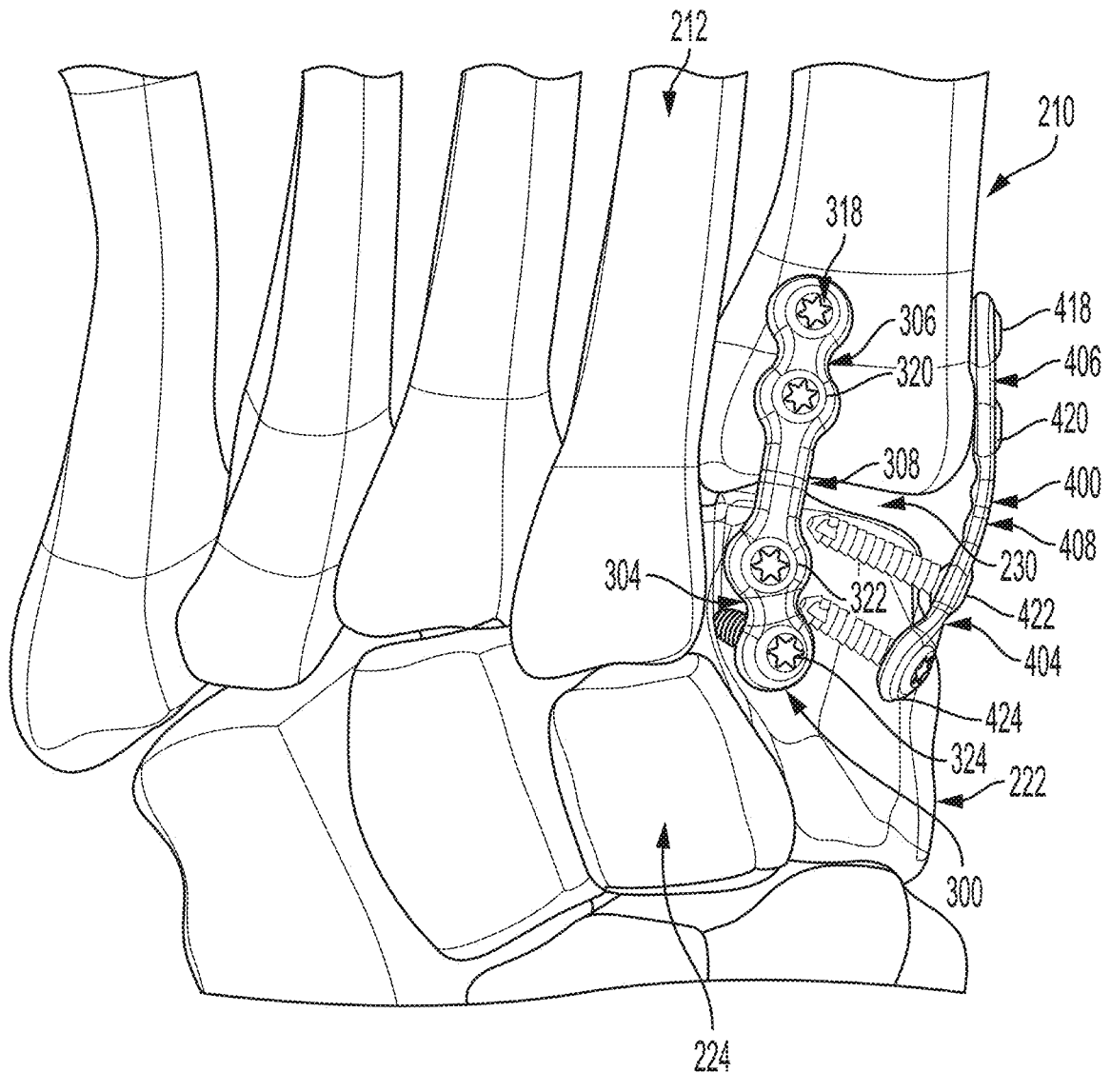
Figure 7B:
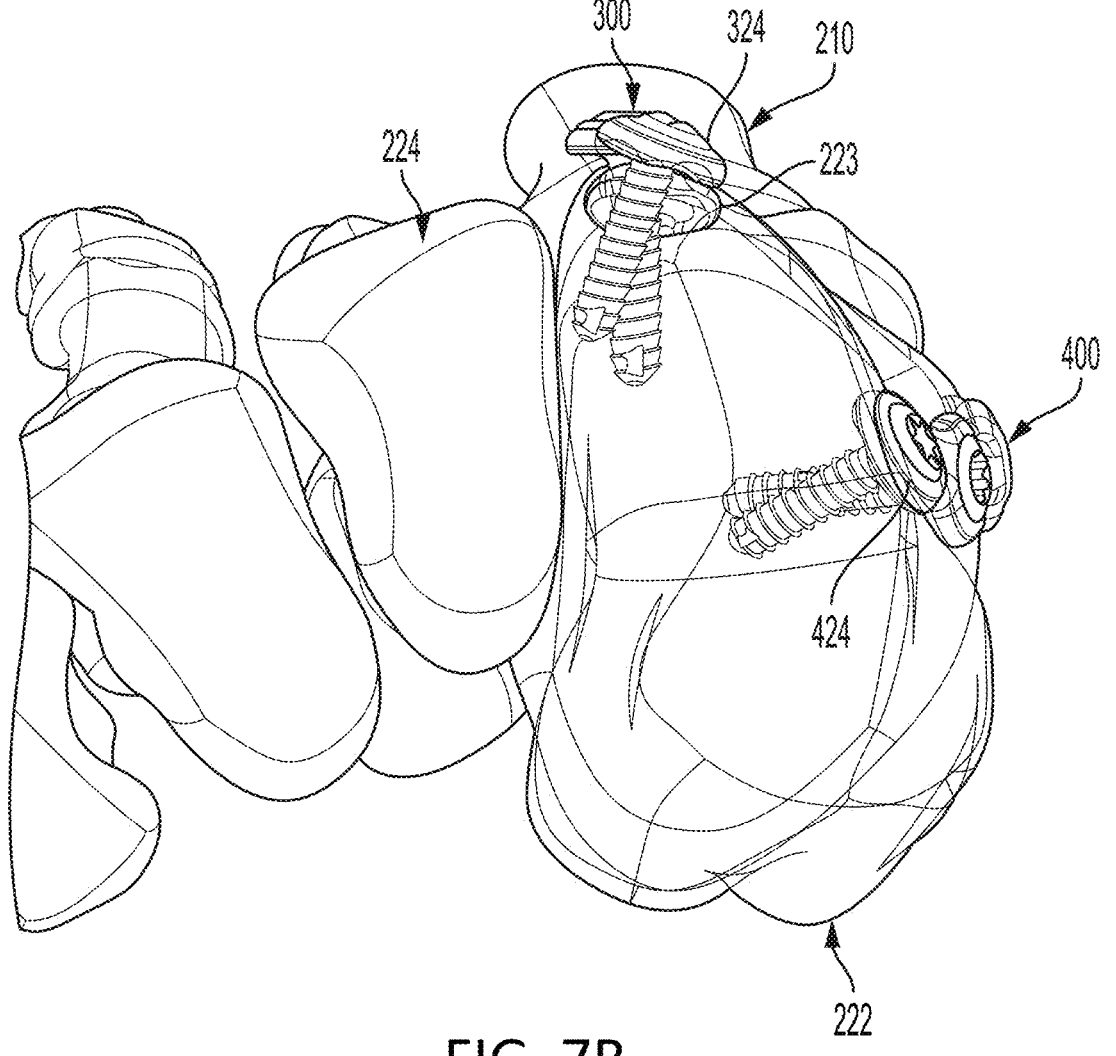
Figure 7C:
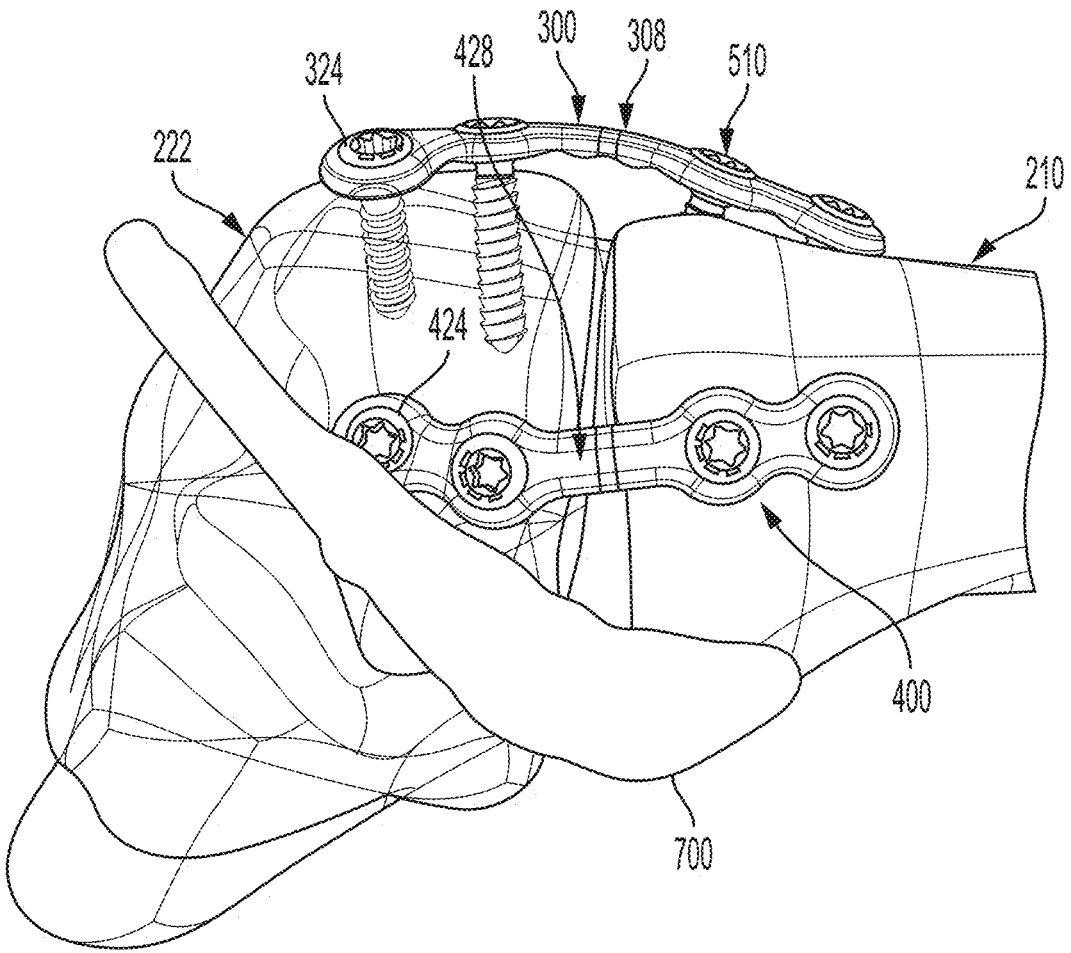

13 ment and fusion procedure, where fixation of one or more bones is desired at two different locations, at these one or more bones, having generally inverse anatomic surface geometries (as is described further in reference to FIGS. 7A-7C). In some such examples, bone plate 400 itself can be a mirror image of bone plate 300.

As described previously herein in reference to FIG. 4, bone plate 300 can include body 302 having four fixation holes, including first fixation hole 318 and second fixation hole 320 separated from third fixation hole 322 and fourth fixation hole 324 by bridge 308. Bone plate 300 can be configured to position first fixation hole 318 and second fixation hole 320 on a dorsal side of a metatarsal and third fixation hole 322 and fourth fixation hole 324 on the dorsal side of a cuneiform, with bridge 308 crossing the dorsal side of a tarsometatarsal joint space between the metatarsal and the cuneiform (as can be seen at FIGS. 7A-7C). First, second, and third fixation holes 318, 320, 322 can be co-linearly aligned with bridge 308, and fourth fixation hole 324 can be angled medially in a transverse plane and rotated plantarly on a frontal plane relative to first, second, and third fixation holes 318, 320, 322 (as can be seen at FIGS. 7A-7C).

Bone plate 400 includes a body 402 having four fixation holes, including a first fixation hole 418 and a second fixation hole 420 separated from a third fixation hole 422 and a fourth fixation hole 424 by a bridge 408. As noted, in some examples, bone plate 400 can have fourth fixation hole 424 offset from bridge central longitudinal axis 410 in an orientation that is a mirror image of the orientation at which fourth fixation hole 324 of bone plate 300 is offset from bridge central longitudinal axis 310. Thus, bone plate 400 can be configured to position third fixation hole 422 and fourth fixation hole 424 on the medial side of the cuneiform, with first fixation hole 418 and second fixation hole 420 on a medial side of the metatarsal and bridge 408 crossing the medial side of the tarsometatarsal joint space between the metatarsal and the cuneiform. First, second, and third fixation holes 418, 420, 422 can be co-linearly aligned with bridge 408, and fourth fixation hole 424 can be angled dorsally in a sagittal plane and rotated laterally in the transverse plane relative to first, second, and third fixation holes 418, 420, 422 (as can be seen at FIGS. 7A-7C).

In some cases, more than just the offset orientation of fourth fixation hole 424 of bone plate 400 can be a mirror image of bone plate 300. For example, bone plate 400 itself can be a mirror image of bone plate 300. In this example, bone plate 300 can be configured to wrap plantarly downward from the dorsal side of the cuneiform, while bone plate 400 can be configured to wrap dorsally upward from the medial side of the cuneiform.

As described previously with respect to bone plate 300, bone plate 300 can have a portion of proximal body region 304, defining fourth fixation hole 324, that includes a plate bend of body 302 deviating from the bridge central longitudinal axis 310 in the first plane by the first plane angle. More specifically, the portion of proximal body region 304 that includes the plate bend of body 302 deviating first fourth fixation hole axis 325 from bridge central longitudinal axis 310 in the first plane by the first plane angle.

Bone plate 400 can include a bend of body 402 that is a mirror image of the bend of body 302 of bone plate 300. Fourth fixation hole 424 can define a first fourth fixation hole axis 425 along which fourth fixation hole 424 extends generally between distal edge 440 of fourth fixation hole 424 and proximal edge 443 of fourth fixation hole 424. And, the portion of proximal body region 404 can include the bend of body 402 in an orientation that deviates first fourth fixation hole axis 425 from bridge central longitudinal axis 410 in the first plane by first plane angle 446. As compared to the bend of body 302 of bone plate 300, the portion of proximal body region 404, of body 402 of bone plate 400, that includes the plate bend of body 402 deviating first fourth fixation hole axis 425 from bridge central longitudinal axis 410 in a first plane by a first plane angle can be a mirror image of the bend of body 302 of bone plate 300 in the first plane by the first angle. First plane angle 446 can be at an angular range as that noted for first plane angle 346 with respect to bone plate 300.

As also described previously with respect to bone plate 300, bone plate 300 can have fourth fixation hole 324 defining second fourth fixation hole axis 327 along which fourth fixation hole 324 extends through body 302 from top surface 314 to bone facing surface 316. The portion of proximal body region 304 defining fourth fixation hole 324 can include the twist of body 302 deviating second fourth fixation hole axis 327 from bridge central longitudinal axis 310 in the second plane by the second plane angle.

Bone plate 400 can include a twist of body 402 that is a mirror image of the twist of body 302 of bone plate 300. Fourth fixation hole 424 can define a second fourth fixation hole axis 427 (axis 427 is shown at FIG. 4B for reference in comparison to axis 327) along which fourth fixation hole 424 extends through body 402 from top surface 414 to bone facing surface 416. And, the portion of proximal body region 404 can include the twist of body 402 in an orientation that deviates second fourth fixation hole axis 427 from bridge central longitudinal axis 410 in the second plane by second plane angle 447. As compared to the twist of body 302 of bone plate 300, the portion of proximal body region 404, of body 402 of bone plate 400, that includes the plate twist of body 402 deviating second fourth fixation hole axis 427 from bridge central longitudinal axis 410 in a second plane by a second plane angle can be a mirror image of the twist of body 302 of bone plate 300 in the second plane by the second angle. Second plane angle 447 can be at an angular range as that noted for second plane angle 347 with respect to bone plate 300. As such, in some examples, bone plate 400 can include the bend of body 402 and twist of body 402 that are each a mirror image of the bend of body 302 and twist of body 302 of bone plate 300.

As noted, kit 500 can include the fixation screws 510 within the sterile container 505. Fixation screws 510 can be locking and/or non-locking fixation screws. In examples, where fixation screws 510 are locking screws, each of fixation screws 510 can include threading 511 at a screw head 512 of each of the fixation screws 510. And, each of the first fixation hole 318, second fixation hole 320, third fixation hole 322, and fourth fixation hole 324 of bone plate 300 can include threading 311, and each of the first fixation hole 418, second fixation hole 420, third fixation hole 422, and fourth fixation hole 424 of bone plate 400 can include threading 411. Threading 311, 411 at fixation holes of bone plates 300, 400 can be complementary to threading 511 at screw head 512 of fixation screws 510 such that the threading 511 can lockingly engage the respective threading 311, 411. As such, screw head 512 of each of fixation screws 510 can be configured to lock to a respective one of first fixation hole 318, the second fixation hole 320, the third fixation hole 322, and the fourth fixation hole 324 of bone plate 300 as well as first fixation hole 418, second fixation hole 420, third fixation hole 422, and fourth fixation hole 424 of bone plate 400.

Figure 6:
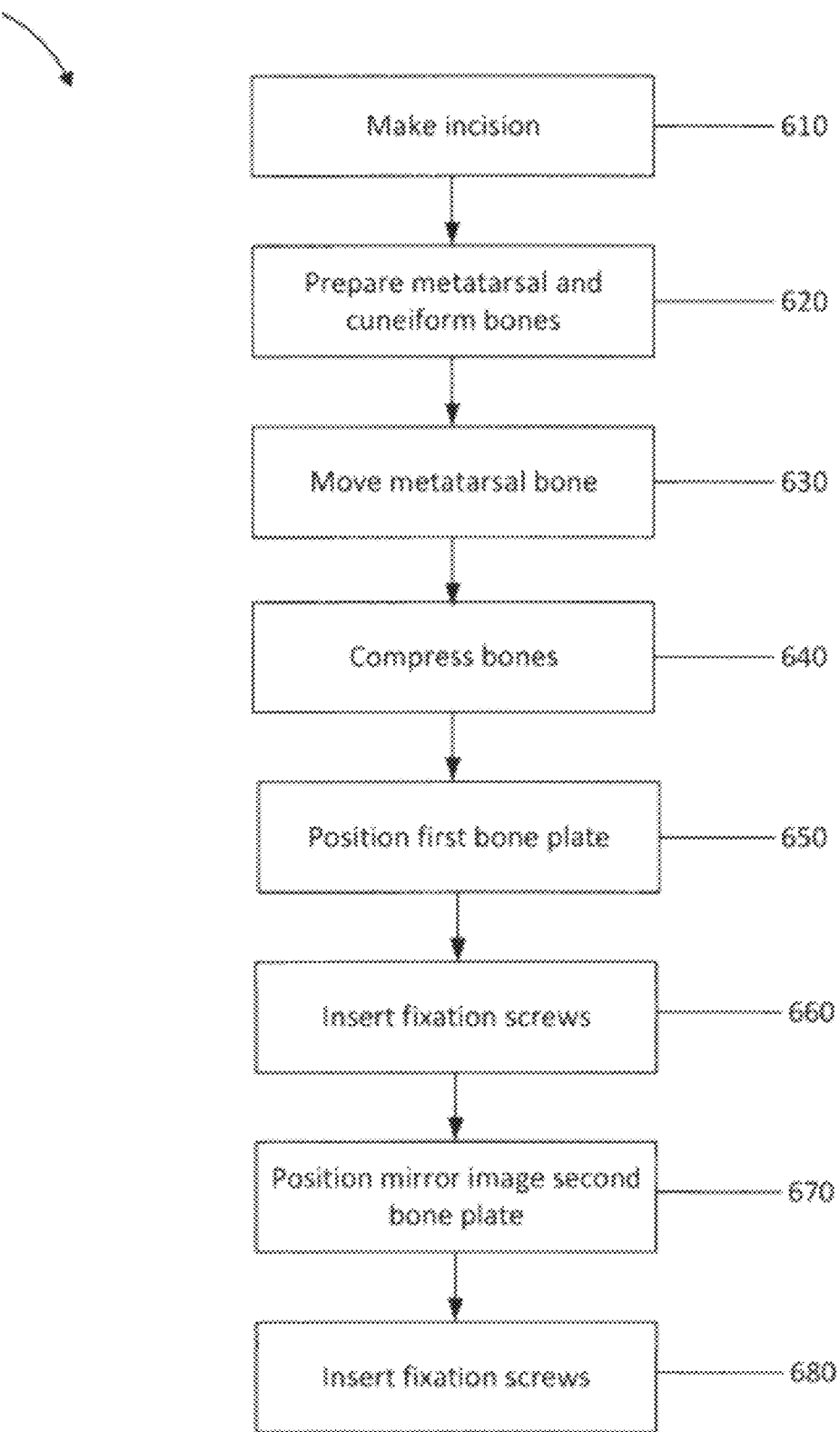

FIG. 6 is a flow diagram of an embodiment of a method 600 that can include, among other steps, positioning and fixating bone plates. As will be described, in one example the method 600 can be used to prepare, realign, and fixate a tarsometatarsal joint. Certain features of the method 600 will be described with reference to FIGS. 7A-7C. Additional details on example surgical techniques, including example instrumentation that can be used during the techniques, can be found in U.S. Pat. No. 9,622,805, issued Apr. 18, 2017 and entitled "BONE POSITIONING AND PREPARING GUIDE SYSTEMS AND METHODS" and US Patent Publication No. 2020/0015856, published Jan. 16, 2020 and entitled "COMPRESSOR-DISTRACTOR FOR ANGULARLY REALIGNING BONE PORTIONS," the entire contents of each of which are incorporated herein by reference.

At step 610, the method 600 includes making an incision. The incision can be made through the skin, such as on a dorsal side of the foot, a medial side of the foot, or on a dorsal-medial side of the foot. The incision can be made to provide surgical access to the TMT joint 230 which separates first metatarsal 210 from opposed medial cuneiform 222. To surgically access the joint, the patient may be placed in a supine position on the operating room table and general anesthesia or monitored anesthesia care administered. Hemostasis can be obtained by applying thigh tourniquet or mid-calf tourniquet. In some examples, imaging of the foot can be used to assist the clinician in ascertaining the location of TMT joint 230 about which incision can be centered when subsequently cutting through skin.

At step 620, the method 600 includes preparing first metatarsal 210 and/or medial cuneiform 222. With the TMT joint 230 exposed via the incision, an end face (e.g., proximal end face) of first metatarsal 210 and/or an end face (e.g., distal end face) of medial cuneiform 222 can be prepared. It is to be noted that one or both of the end faces of the metatarsal and the cuneiform can be prepared before and/or after the metatarsal is moved relative to the cuneiform. Accordingly, unless otherwise specified, the order of bone preparation and/or movement is not limited. In general, the clinician can prepare the end of each bone forming TMT joint 230 so as to promote fusion of the bone ends across the TMT joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a bone preparation guide, a cutting instrument can be inserted against a guide surface (e.g., between a slot define between two guide surfaces) of the bone preparation guide to guide the cutting instrument for bone removal.

At step 630, the method 600 includes moving first metatarsal 210. As noted, first metatarsal 210 can be moved before and/or after first metatarsal 210 and/or medial cuneiform 222 are prepared. Moving first metatarsal 210 at step 630 can include moving first metatarsal 210 in at least one plane. For example, first metatarsal 210 can be moved in at least transverse plane to close IMA 234 between first metatarsal 210 and adjacent second metatarsal 212 and/or a frontal plane (e.g., to reposition the sesamoid bones substantially centered under the metatarsal). In some examples, first metatarsal 210 can be moved in multiple planes, such as the transverse plane and/or frontal plane and/or sagittal plane (e.g., each of the transverse, frontal, and sagittal planes). The clinician may or may not utilize a bone positioning device to facilitate movement of the bone portion. The moved position of first metatarsal 210 can result is realignment of first metatarsal 210 relative to one of more other adjacent bones.

At step 640, the method 600 may include compressing one or more bones. In some embodiments, the step 640 can be omitted depending on the realigned position of the first metatarsal 210. When step 640 is included, the prepared end faces of the bone portions of first metatarsal 210 and medial cuneiform 222 can be compressed together prior to fixating one or more plates at these bones. The clinician may compress the end faces together with hand pressure and/or using a compressing instrument physically attached to both the first bone portion and the second bone portion.

At step 650, the method 600 includes positioning bone plate (e.g., a first bone plate) 300 over a portion of first metatarsal 210 and over a portion of medial cuneiform 222 and across TMT joint 230 separating metatarsal 210 from cuneiform 222. For example, as shown at FIGS. 7A-7C, positioning a bone plate at step 650 can include positioning bone plate 300. Positioning bone plate 300 can include positioning first fixation hole 318 and second fixation hole 320 over metatarsal 210 and positioning third fixation hole 322 and fourth fixation hole 324 over cuneiform 222 with bridge 308 separating second fixation hole 320 from third fixation hole 322 extending across the TMT joint 230. As described previously herein with respect to bone plate 300, first, second, and third fixation holes 318, 320, 322 can be arranged co-linearly with the bridge central longitudinal axis defined by bridge 308, and fourth fixation hole 324 can be offset from the bridge central longitudinal axis in a first plane by a first plane angle and in a second plane by a second plane angle. In some examples, positioning bone plate 300 at step 650 can include positioning distal body region 306 of bone plate 300 at metatarsal 210 and positioning proximal body region 304 of bone plate 300 at cuneiform 222.

At step 660, the method 600 includes inserting fixation screw 510 through each of first fixation hole 318 and the second fixation hole 320 into the underlying metatarsal 210 and through each of third fixation hole 322 and fourth fixation hole 324 into the underlying cuneiform 222.

As shown at FIGS. 7A-7C, bone plate 300 can be secured at the dorsal side of metatarsal 210, the dorsal side of cuneiform 222, and across the dorsal side of TMT joint 230 (e.g., the dorsal side of the joint space between metatarsal 210 and cuneiform 222). As also shown at FIGS. 7A-7C, bone plate 300 can be positioned and secured so as to wrap plantarly downward from the dorsal side of the cuneiform 222. In particular, the offset orientation of fourth fixation hole 324 can generally wrap plantarly downward from the dorsal side of the cuneiform 222. As can be seen at FIGS. 7A-7C, this feature provides bone plate 300 with an anatomic fit suited for medial cuneiform 222. For instance, the described bend of body 302 of plate 300 can position fourth fixation hole 324 to be spaced apart from the joint space between cuneiform 222, metatarsal 212, and cuneiform 224. In this way, the bend of body 302 of plate 300 can position fourth fixation hole 324 to generally follow the shape of cuneiform 222 so as to position fourth fixation hole 324 over cuneiform 222 and away from the joint space between cuneiform 222, metatarsal 212, and cuneiform 224. In addition, the described twist of body 302 of plate 300 can position fourth fixation hole 324 to lay generally flush against the dorsal surface 223, of cuneiform 222, that slopes downward in a medial direction. Accordingly, these features of bone plate 300 can facilitate an anatomic fit at cuneiform 222 by generally tracking the native surface contouring at cuneiform 222.

In some embodiments, fixation screws can be inserted into bone plate 300 in a particular order. As one such example, where second fixation hole 320 is positioned closer to bridge 308 than first fixation hole 318 and third fixation hole 322 is positioned closer to bridge 308 than fourth fixation hole 324, a first fixation screw can be inserted through second fixation hole 320 and a second fixation screw can be inserted through third fixation hole 322. Then, after the first fixation screw is inserted through second fixation hole 320 and the second fixation screw is inserted through third fixation hole 322, a third fixation screw can be inserted through first fixation hole 318 and a fourth fixation screw can be inserted through fourth fixation hole 324. As another such example, also where second fixation hole 320 is positioned closer to bridge 308 than first fixation hole 318 and third fixation hole 322 is positioned closer to bridge 308 than fourth fixation hole 324, a first fixation screw can be inserted through first fixation hole 318 and a second fixation screw can be inserted through fourth fixation hole 324. Then, after the first fixation screw is inserted through first fixation hole 318 and the second fixation screw is inserted through fourth fixation hole 324, a third fixation screw can be inserted through second fixation hole 320 and a fourth fixation screw can be inserted through third fixation hole 322.

At step 670, the method 600 includes positioning a second bone plate 400 over a portion of first metatarsal 210 and over a portion of medial cuneiform 222 and across TMT joint 230 separating metatarsal 210 from cuneiform 222. Second bone plate 400 can be a mirror image of bone plate 300. Positioning bone plate 400 can include positioning first fixation hole 418 and second fixation hole 420 over metatarsal 210 and positioning third fixation hole 422 and fourth fixation hole 424 over cuneiform 222 with bridge 408 separating second fixation hole 420 from third fixation hole 422 extending across TMT joint 230. As described previously herein with respect to bone plate 400, first, second, and third fixation holes 418, 420, 422 can be arranged co-linearly with the bridge central longitudinal axis defined by bridge 408, and fourth fixation hole 424 can be offset from the bridge central longitudinal axis in a first plane by a first plane angle and in a second plane by a second plane angle. In some examples, positioning bone plate 400 at step 670 can include positioning distal body region 406 of bone plate 400 at metatarsal 210 and positioning proximal body region 404 of bone plate 400 at cuneiform 222.

At step 680, the method 600 includes inserting fixation screw 510 through each of first fixation hole 418 and the second fixation hole 420 into the underlying metatarsal 210 and through each of third fixation hole 422 and fourth fixation hole 424 into the underlying cuneiform 222.

As shown at FIGS. 7A-7C, bone plate 400 can be secured at the medial side of metatarsal 210, the medial side of cuneiform 222, and across the medial side of TMT joint 230

(e.g., the dorsal side of the joint space between metatarsal 210 and cuneiform 222). As also shown at FIGS. 7A-7C, bone plate 400 can be positioned and secured so as to wrap dorsally upward from the medial side of cuneiform 222. In particular, the offset orientation of fourth fixation hole 424 can generally wrap dorsally upward from the medial side of cuneiform 222. As can be seen at FIGS. 7A-7C, this feature provides bone plate 400 with an anatomic fit suited for medial cuneiform 222 and/or one or more adjacent tendons. For instance, as best seen at FIG. 7C, a tendon, referred to as the tibialis anterior tendon, 700 can sweep across the medial side of cuneiform 222 and interfere with access to the fixation surface at cuneiform 222. The configuration of bone plate 400, including the described bend and twist of body 402, can provide an anatomic fit at cuneiform 222 that diverges the fourth fixation hole 424 from the bridge central longitudinal axis in a dorsal direction along cuneiform 222 and in a direction laterally away from tend 700 to thereby help reduce interference posed by the tendon 700 and, likewise, reduce instances of damage to tendon 700 during a surgical procedure using bone plate 400. Also, the configuration of bone plate 400, including the described bend and twist of body 402, can position fourth fixation hole 424 to generally follow the shape of cuneiform 222 at the medial side so as to position fourth fixation hole 424 over cuneiform 222 at an orientation that generally tracks, and is generally flush with, the slope at the medial surface of cuneiform 222. Accordingly, these features of bone plate 400 can facilitate an anatomic fit at cuneiform 222 by generally tracking the native surface contouring at cuneiform 222 and generally diverges from the native, adjacent tendon trajectory.

In some embodiments, fixation screws can be inserted into bone plate 400 in a particular order. As one such example, where second fixation hole 420 is positioned closer to bridge 408 than first fixation hole 418 and third fixation hole 422 is positioned closer to bridge 408 than fourth fixation hole 424, a first fixation screw can be inserted through second fixation hole 420 and a second fixation screw can be inserted through third fixation hole 422. Then, after the first fixation screw is inserted through second fixation hole 420 and the second fixation screw is inserted through third fixation hole 422, a third fixation screw can be inserted through first fixation hole 418 and a fourth fixation screw can be inserted through fourth fixation hole 424. As another such example, also where second fixation hole 420 is positioned closer to bridge 408 than first fixation hole 418 and third fixation hole 422 is positioned closer to bridge 408 than fourth fixation hole 424, a first fixation screw can be inserted through first fixation hole 418 and a second fixation screw can be inserted through fourth fixation hole 424. Then, after the first fixation screw is inserted through first fixation hole 418 and the second fixation screw is inserted through fourth fixation hole 424, a third fixation screw can be inserted through second fixation hole 420 and a fourth fixation screw can be inserted through third fixation hole 422.

Figure 8A:
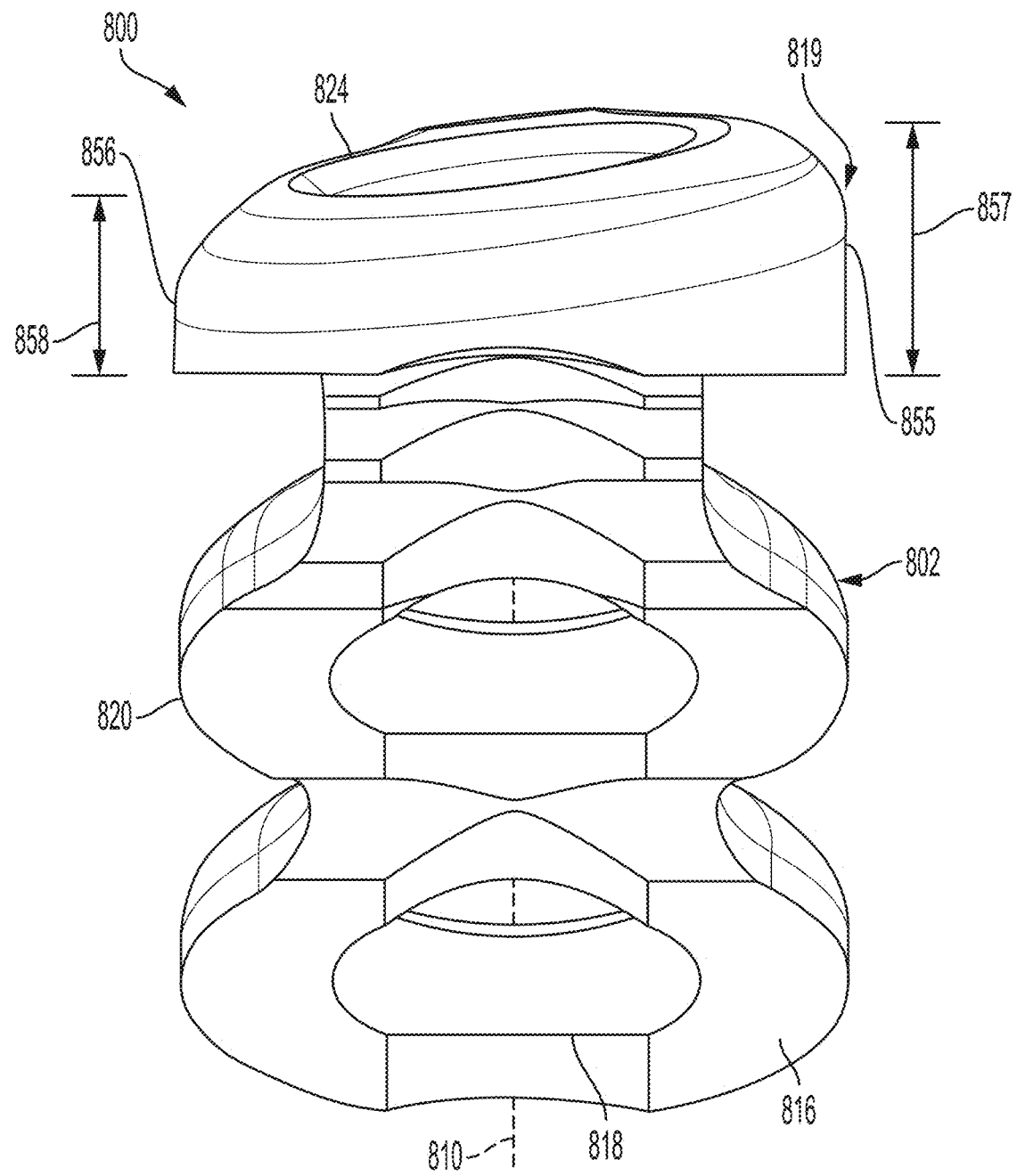
Figures 8B, 8C:
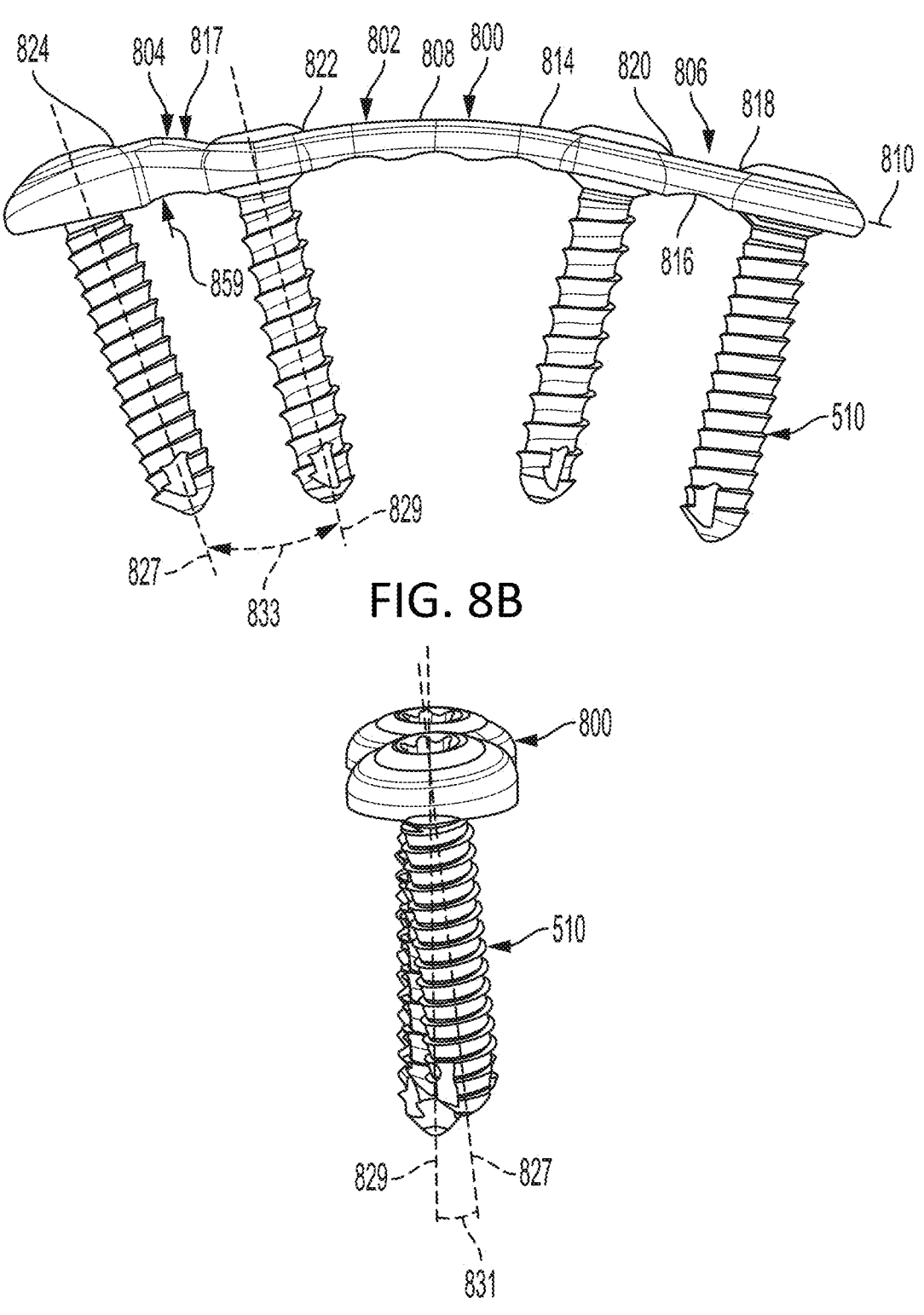

FIGS. 8A-8C show another embodiment of a bone plate 800. FIG. 8A is a perspective view of bone plate 800, FIG. 8B is a side elevational view of bone plate 800 including fixation screws 510, and FIG. 8C is an end elevational view of bone plate 800 including fixation screws 510.

Bone plate 800 can include a body 802 that includes a proximal body region 804 configured to be positioned over a cuneiform (e.g., a medial cuneiform), a distal body region 806 configured to be positioned over a metatarsal (e.g., a first metatarsal), and a bridge 808 extending between proximal body region 804 and distal body 806 region. Bridge 808 is configured to be positioned across a tarsometatarsal joint (e.g., first tarsometatarsal joint) separating the metatarsal from the cuneiform. Bridge 808 defines a bridge central longitudinal axis 810. Body 802 has a width defining an extent of bone plate 800 transverse to bridge central longitudinal axis 810. Body 802 includes a top surface 814 and a bone facing surface 816 opposite the top surface.

Body 802 can include multiple fixation holes. In the illustrated embodiment, body 802 includes a first fixation hole 818 and a second fixation hole 820 located in distal body region 806, and each of first fixation hole 818 and second fixation hole 820 is positioned co-linear with bridge central longitudinal axis 810. First fixation hole 818 and second fixation hole 820 each extend through body 802 from top surface 814 to bone facing surface 816, and each of first fixation hole 818 and second fixation hole 820 is configured to receive fixation screw 510 therethrough. Also in the illustrated embodiment, body 802 includes a third fixation hole 822 and a fourth fixation hole 824 located in proximal body region 804, and each of third fixation hole 822 and fourth fixation hole 824 is positioned co-linear with bridge central longitudinal axis 810. Thus, for bone plate 800, each of first, second, third, and fourth fixation holes 818, 820, 822, and 824 can intersect bridge central longitudinal axis 810. Third fixation hole 822 and fourth fixation hole 824 each extend through body 802 from top surface 814 to bone facing surface 816, and each of third fixation hole 822 and fourth fixation hole 824 is configured to receive fixation screw 510 therethrough.

Fourth fixation hole 824 can have a profile that differs from a profile of each of first, second, and third fixation holes 818, 820, and 822. In particular, fourth fixation hole 824 can have a first skewed profile 819 relative to the profile of each of first, second, and third fixation holes 818, 820, and 822. For example, a portion of body 802 defining fourth fixation hole 824 can have a non-uniform height that creates first skewed profile 819. As seen best at FIG. 8A, the portion of body 802 defining fourth fixation hole 824 can have a first lateral body side 855 and a second, opposite lateral body side 856. First lateral body side 855 can have a first height 857 and second lateral body side 856 can have a second height 858 that is different than the first height 857. In the illustrated embodiment, the first height 857 is greater than the second height 858, though in another embodiment the second height 858 can be greater than the first height 857.

This difference is height at the opposite lateral sides 855, 856 of the portion of body 802 defining fourth fixation hole 824 can create, at least in part, first skewed profile 819, and first skewed profile 819 can result in a first skewed trajectory of a fixation screw inserted though fourth fixation hole 824 relative to a fixation screw inserted through each of first, second, and third fixation holes 818, 820, and 822. In particular, fourth fixation hole 824 defines a fourth fixation hole axis 827 along which fourth fixation hole 824 extends through body 802 from top surface 814 to bone facing surface 816, and third fixation hole 822 defines a third fixation hole axis 829 along which third fixation hole 822 extends through body 802 from top surface 814 to bone facing surface 816. As best seen in the frontal plane view shown at FIG. 8C, fourth fixation hole axis 827 is skewed relative to third fixation hole axis 829 in a first plane by a first plane angle. Specifically, fourth fixation hole axis 827 can be skewed in a frontal plane relative to third fixation hole axis 829 by an angle 831 ranging from 1° to 20°, from 5° to 15°, or from 7° to 12°.

In addition, fourth fixation hole 824 can have a second skewed profile 817 relative to the profile of each of first, second, and third fixation holes 818, 820, and 822. Second skewed profile 817 can skew fourth fixation hole 824 in a second plane, different than the first plane, by a second plane angle. For example, a portion of body 802 at proximal body region 804 and longitudinally between fourth fixation hole 824 and third fixation hole 822 can create second skewed profile 817. In the illustrated embodiment, portion of body 802 at proximal body region 804 and longitudinally between fourth fixation hole 824 and third fixation hole 822 create second skewed profile 817 by increasing in height 859 relative to a height of body 802 at bridge 808 and a height longitudinally between second fixation hole 820 and first fixation hole 818.

Second skewed profile 817 can result in a second skewed trajectory, different than the first skewed trajectory resulting from first skewed profile 819, of a fixation screw inserted though fourth fixation hole 824 relative to a fixation screw inserted through each of first, second, and third fixation holes 818, 820, and 822. In particular, as noted, fourth fixation hole 824 defines fourth fixation hole axis 827 along which fourth fixation hole 824 extends through body 802 from top surface 814 to bone facing surface 816, and third fixation hole 822 defines third fixation hole axis 829 along which third fixation hole 822 extends through body 802 from top surface 814 to bone facing surface 816. As best seen in the sagittal plane view shown at FIG. 8B, fourth fixation hole axis 827 is skewed relative to third fixation hole axis 829 in a second plane by a second plane angle. Specifically, fourth fixation hole axis 827 can be skewed in a sagittal plane relative to third fixation hole axis 829 by an angle 833 ranging from 1° to 20°, from 5° to 15°, or from 7° to 12°.

Skewed profiles 817, 819 of fourth fixation hole 824 can help to fit bone plate 800 to the native bone anatomy at which bone plate 800 is to be positioned and fixated. For example, in an application where bone plate 800 is configured to have proximal body region 804 positioned at a cuneiform (e.g., medial cuneiform), skewed profiles 817, 819 of fourth fixation hole 824 can be configured to angle a fixation screw inserted through fourth fixation hole 824 away from a joint space adjacent the cuneiform. This, in turn, can facilitate more robust securement of proximal body region 804 at the cuneiform.

Figure 9A:
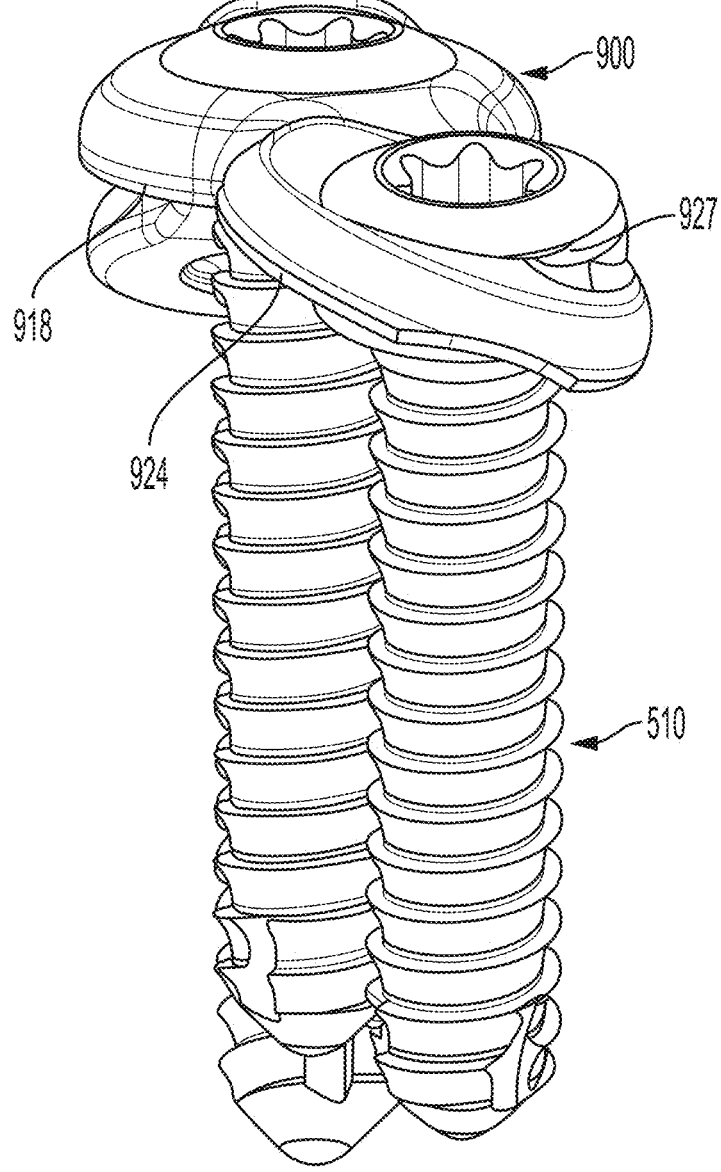
Figure 9B:
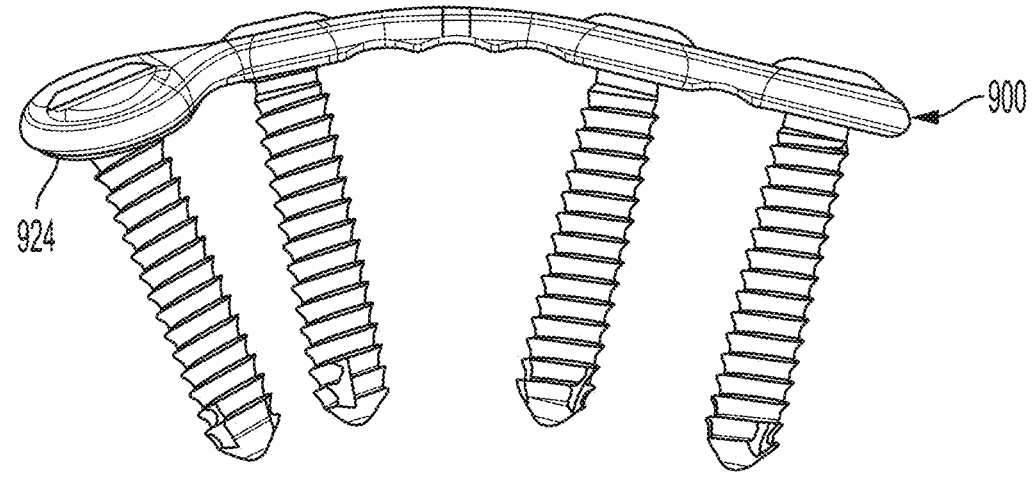
Figure 9C:
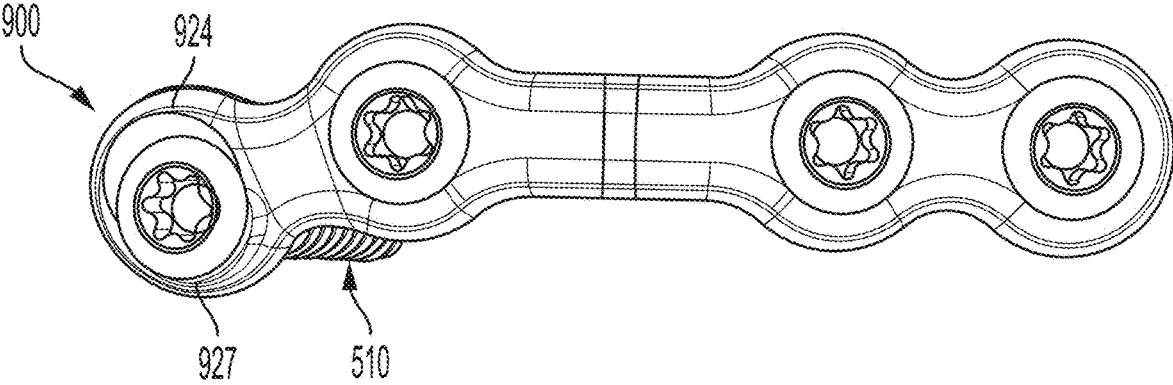

FIGS. 9A-9C show an additional embodiment of a bone plate 900. In particular, FIG. 9A illustrates an end (e.g., proximal end) elevational view of the bone plate 900 with fixation screws 510, FIG. 9B is side elevational view of the bone plate with fixation screws 510, and FIG. 9C is a top plan view of the bone plate with fixation screws 510.

The illustrated embodiment of the bone plate 900 can include a fixation hole (e.g., a third fixation hole) 918 and a fixation hole (e.g., a fourth fixation hole) 927 at a same side of a bridge of the bone plate 900. Each of the fixation hole 918 and the fixation hole 927 can define a fixation screw axis extending therethrough and along which fixation screw axis the fixation screw 510 extends when placed at the respective fixation hole 918, 927. As shown here, the fixation hole 918 can be configured to define the fixation screw axis that is parallel (e.g., substantially parallel) to at least the fixation screw axis defined by the fixation hole 927 such that the fixation screws 510, extending through the fixation holes 918, 927, are generally parallel to one another when placed at the fixation holes 918, 927. In addition, a bone plate surface 924, of the bone plate 900, that defines the fixation hole 927 can be skewed relative to the bone plate surface that defines the fixation hole 918. For example, the bone plate surface 924 that defines the fixation hole 927 can be skewed, relative to the bone plate surface that defines the fixation hole 918, at an angle ranging from 5° to 50°, such as ranging from 10° to 40°, ranging from 15° to 35°, or ranging from 20° to 25°. This angularly skewed orientation of the bone plate surface 924 that defines the fixation hole 927, relative to the bone plate surface that defines the fixation hole 918, can help to prevent fixation screw(s) 510 from being inserted into unintended anatomical locations, for instance helping to prevent fixation screw(s) 510 from being inserted into the intercuneiform space, yet while maintaining bone plate surface conformity to the anatomical geometry/shape of the first cuneiform (e.g., in both dorsal and medial directions at the first cuneiform).

A bone plate as described herein may be used alone or in combination with one or other bone fixation devices to fixate a joint between opposed bone portions for fusion. Other types of bone fixation devices that can be used include, but are not limited to, a bone screw (e.g., a compressing bone screw), a bone plate (e.g., having a different configuration than an anatomically configured bone plate as described herein), a bone staple, an external fixator, a pin (e.g., an intramedullary implant), and/or combinations thereof. A bone plate according to the disclosure can be attached before or after installing the one or more other bone fixation devices (when used) to the bone portions being fixated.

Various examples have been described. These and other examples are within the scope of the following claims.

The invention claimed is:

1. A method of fixating a tarsometatarsal joint, the method comprising:

positioning a bone plate over a portion of a metatarsal and over a portion of a cuneiform and across a tarsometatarsal joint separating the metatarsal from the cuneiform, wherein positioning the bone plate comprises positioning a first fixation hole and a second fixation hole over a dorsal side of the metatarsal and positioning a third fixation hole and a fourth fixation hole over a dorsal side the cuneiform with a bridge separating the second fixation hole from the third fixation hole extending across a dorsal side the tarsometatarsal joint, wherein the first, second, and third fixation holes are arranged co-linearly with a bridge central longitudinal axis defined by the bridge and the fourth fixation hole is offset from the bridge central longitudinal axis in a first plane by a first plane angle and in a second plane by a second plane angle such that the fourth fixation hole is positioned at the dorsal side of the cuneiform; and inserting a fixation screw through each of the first fixation hole and the second fixation hole into the underlying metatarsal and through each of the third fixation hole and the fourth fixation hole into the underlying cuneiform.

2. The method of claim 1, further comprising the steps of: securing a second plate distal body region of a second bone plate at the metatarsal via at least one of a second plate first fixation hole and a second plate second fixation hole that are defined at the second plate distal body region; and securing a second plate proximal body region of the second bone plate at the cuneiform via at least one of a second plate third fixation hole and a second plate fourth fixation hole that are defined at the second plate proximal body region, wherein the second plate is a mirror image of the first plate.

3. The method of claim 2, wherein:

the metatarsal is a first metatarsal and the cuneiform is a medial cuneiform;

the laterally-adjacent metatarsal is a second metatarsal and the laterally-adjacent cuneiform is an intermediate cuneiform;

the first bone plate is secured at the dorsal side of the first metatarsal, the dorsal side of the medial cuneiform, and across the dorsal side of a tarsometatarsal joint between the first metatarsal and the medial cuneiform; and the first bone plate is secured so as to wrap plantarly downward from the dorsal side of the medial cuneiform to deviate the fourth fixation hole away from an inter-metatarsal joint space between the first metatarsal and second metatarsal and/or an intercuneiform joint space between the medial cuneiform and the intermediate cuneiform.

4. The method of claim 3, wherein the second bone plate is secured at a medial side of the first metatarsal, a medial side of the intermediate cuneiform, and across a medial side of the tarsometatarsal joint between the first metatarsal and the medial cuneiform, and wherein the second bone plate is secured so as to wrap dorsally upward from the medial side of the medial cuneiform.

5. The method of claim 1, wherein:

the second fixation hole is positioned closer to the bridge than the first fixation hole, and the third fixation hole is positioned closer to the bridge than the fourth fixation hole, a first fixation screw is inserted through the second fixation hole and a second fixation screw is inserted through the third fixation hole, and after the first fixation screw is inserted through the second fixation hole and the second fixation screw is inserted through the third fixation hole, a third fixation screw is inserted through the first fixation hole and a fourth fixation screw is inserted through the fourth fixation hole.

6. The method of claim 1, wherein:

the second fixation hole is positioned closer to the bridge than the first fixation hole, and the third fixation hole is positioned closer to the bridge than the fourth fixation hole, a first fixation screw is inserted through the first fixation hole and a second fixation screw is inserted through the fourth fixation hole, and after the first fixation screw is inserted through the first fixation hole and the second fixation screw is inserted through the fourth fixation hole, a third fixation screw is inserted through the second fixation hole and a fourth fixation screw is inserted through the third fixation hole.

7. The method of claim 1, wherein:

the bone plate comprises a proximal body region, a distal body region, and the bridge extending between the proximal body region and the distal body region;

the body has a width defining an extent of the bone plate transverse to the bridge central longitudinal axis, and includes a top surface and a bone facing surface opposite the top surface;

the first fixation hole and the second fixation hole are located in the distal body region; and the third fixation hole and the fourth fixation hole are located in the proximal body region, and the third fixation hole is positioned closer to the bridge than the fourth fixation hole.

8. The method of claim 7, wherein the second fixation hole is positioned closer to the bridge than the first fixation hole, the bridge defines a length extending from an edge of the second fixation hole to an edge of the third fixation hole, and the length of the bridge has a midline halfway between the edge of the second fixation hole and the edge of the third fixation hole; and a body of the bone plate defines a proximal length extending from the midline of the bridge to a proximal edge of the bone plate, and the proximal length is less than 19 mm.

9. The method of claim 8, wherein the body defines a distal length extending from the midline of the bridge to a distal edge of the bone plate, and a ratio of the distal length divided by the proximal length is greater than 1.0.

10. The method of claim 9, wherein:

the body defines an overall length from the proximal edge to the distal edge ranging from 30-40 mm;

the length of the bridge ranges from 9.0 mm to 15.0 mm;

the proximal length ranges from 17-18.5 mm; and the distal length ranges from 15-18 mm.

11. The method of claim 1, wherein a geometric center of the fourth fixation hole is offset from the bridge central longitudinal axis in the first plane a distance ranging from 1-4 mm.

12. The method of claim 11, wherein the geometric center of the fourth fixation hole is offset from the bridge central longitudinal axis in the second plane at an angle ranging from 5° to 40°, and wherein the geometric center of the fourth fixation hole is offset from the bridge central longitudinal axis in the second plane so as to configure the fourth fixation hole to receive the fixation screw therethrough and maintain the fixation screw in a substantially parallel orientation relative to at least one other fixation screw received at the bone plate.

13. The method of claim 1, wherein the first plane is a transverse plane and the second plane is a frontal plane.

14. The method of claim 1, wherein:

the bridge defines a length extending from an edge of the second fixation hole to an edge of the third fixation hole;

a distance between the first fixation hole and the second fixation hole defines a first intra-hole spacing; and a ratio of the first intra-hole spacing to the length of the bridge is at least 0.78.

15. The method of claim 14, wherein:

a distance between the third fixation hole and the fourth fixation hole defines a second intra-hole spacing; and a ratio of the second intra-hole spacing to the length of the bridge is at least 0.78.

16. The method of claim 1, wherein a width of a body of the bone plate is greater at locations of the body defining each of the first fixation hole, second fixation hole, third fixation hole, and fourth fixation hole than at the bridge, and wherein the width of the body is less at locations longitudinally between the first fixation hole, second fixation hole, third fixation hole, and fourth fixation hole than at locations of the body defining the first fixation hole, second fixation hole, third fixation hole, and fourth fixation hole.

17. The method of claim 1, wherein the first, second, third, and fourth fixation holes are the only fixation holes provided by the bone plate.

18. The method of claim 1, wherein the fourth fixation hole is positioned at the dorsal side of the cuneiform so as to deviate away from a joint space between the cuneiform and a laterally-adjacent metatarsal and/or laterally-adjacent cuneiform.

19. A method of fixating a tarsometatarsal joint, the method comprising:

positioning a bone plate over a portion of a metatarsal and over a portion of a cuneiform and across a tarsometatarsal joint separating the metatarsal from the cuneiform, wherein positioning the bone plate comprises positioning a first fixation hole and a second fixation hole over the metatarsal and positioning a third fixation hole and a fourth fixation hole over the cuneiform with a bridge separating the second fixation hole from the third fixation hole extending across the tarsometatarsal joint, wherein the first, second, and third fixation holes are arranged co-linearly with a bridge central longitudinal axis defined by the bridge and the fourth fixation hole is offset from the bridge central longitudinal axis in a first plane by a first plane angle and in a second plane by a second plane angle; and inserting a fixation screw through each of the first fixation hole and the second fixation hole into the underlying metatarsal and through each of the third fixation hole and the fourth fixation hole into the underlying cuneiform, wherein the bone plate comprises a proximal body region, a distal body region, and the bridge extending between the proximal body region and the distal body region, wherein the body has a width defining an extent of the bone plate transverse to the bridge central longitudinal axis, and includes a top surface and a bone facing surface opposite the top surface, wherein the first fixation hole and the second fixation hole are located in the distal body region, the third fixation hole and the fourth fixation hole are located in the proximal body region, and the third fixation hole is positioned closer to the bridge than the fourth fixation hole, wherein the second fixation hole is positioned closer to the bridge than the first fixation hole, the bridge defines a length extending from an edge of the second fixation hole to an edge of the third fixation hole, and the length of the bridge has a midline halfway between the edge of the second fixation hole and the edge of the third fixation hole, and wherein a body of the bone plate defines a proximal length extending from the midline of the bridge to a proximal edge of the bone plate, and the proximal length is less than 19 mm.

20. A method of fixating a tarsometatarsal joint, the method comprising:

positioning a bone plate over a portion of a metatarsal and over a portion of a cuneiform and across a tarsometatarsal joint separating the metatarsal from the cuneiform, wherein positioning the bone plate comprises positioning a first fixation hole and a second fixation hole over the metatarsal and positioning a third fixation hole and a fourth fixation hole over the cuneiform with a bridge separating the second fixation hole from the third fixation hole extending across the tarsometatarsal joint, wherein the first, second, and third fixation holes are arranged co-linearly with a bridge central longitudinal axis defined by the bridge and the fourth fixation hole is offset from the bridge central longitudinal axis in a first plane by a first plane angle and in a second plane by a second plane angle; and inserting a fixation screw through each of the first fixation hole and the second fixation hole into the underlying metatarsal and through each of the third fixation hole and the fourth fixation hole into the underlying cuneiform, wherein the bridge defines a length extending from an edge of the second fixation hole to an edge of the third fixation hole, a distance between the first fixation hole and the second fixation hole defines a first intra-hole spacing, and a ratio of the first intra-hole spacing to the length of the bridge is at least 0.78.

\* \* \* \* \*